United States Patent [19]

Cross et al.

[11] Patent Number: 4,806,536
[45] Date of Patent: Feb. 21, 1989

[54] PIPERAZINYL-SUBSTITUTED PYRIDINE AND IMIDAZOLE ANTI-ARRHYTHMIC AGENTS

[75] Inventors: Peter E. Cross, Canterbury; Roger P. Dickinson, Dover, both of England

[73] Assignee: Pfizer, Inc., New York, N.Y.

[21] Appl. No.: 10,077

[22] Filed: Feb. 2, 1987

[30] Foreign Application Priority Data

Feb. 7, 1986 [GB] United Kingdom ............... 8603120

[51] Int. Cl.$^4$ ............... A61K 31/495; C07D 401/04; C07D 403/04
[52] U.S. Cl. ............... 514/252; 544/360; 544/370
[58] Field of Search ............... 544/360, 370; 514/252

[56] References Cited

U.S. PATENT DOCUMENTS

| | | | |
|---|---|---|---|
| 2,927,924 | 3/1960 | Mills | 260/268 |
| 2,979,508 | 4/1961 | Janssen | 260/268 |
| 3,168,522 | 2/1965 | de Stevens et al. | 260/268 |
| 3,341,584 | 9/1967 | Larsen et al. | 564/89 |
| 3,574,741 | 4/1971 | Gould et al. | 564/443 |
| 3,660,487 | 5/1972 | Larsen et al. | 564/99 |
| 3,941,789 | 3/1976 | Renth et al. | 544/360 |
| 4,038,279 | 7/1977 | Renth et al. | 544/295 |
| 4,136,185 | 1/1979 | Renth et al. | 544/295 |
| 4,289,787 | 9/1981 | Molloy et al. | 564/284 |

FOREIGN PATENT DOCUMENTS

| | | |
|---|---|---|
| 0154969 | 9/1985 | European Pat. Off. |
| 0164865 | 12/1985 | European Pat. Off. |
| 1173369 | 12/1969 | United Kingdom |
| 1456253 | 11/1976 | United Kingdom |
| 2053897 | 2/1981 | United Kingdom |

*Primary Examiner*—Donald G. Daus
*Assistant Examiner*—Cecilia Shen
*Attorney, Agent, or Firm*—Peter C. Richardson; Paul H. Ginsburg; Lawrence C. Akers

[57] ABSTRACT

A series of novel 4-substituted piperazinyl-pyridine and 4-substituted piperazinyl-imidazole compounds have been prepared, including their pharmaceutically acceptable salts, wherein the 4-substituent is a lower phenylalkyl group or a derivative thereof further substituted on the phenyl moiety by a sulphamoyl or sulphonylamino group or by a nitro, amino or acetamido group. These particular compounds are useful in therapy as highly effective anti-arrhythmic agents and therefore, are of value in the treatment of various cardiac arrythmias. The most preferred member compound of the series is N-{4-[1-hydroxy-2-(4-[4-pyridinyl]-1-piperazinyl)ethyl]phenyl} methanesulphonamide. Methods for preparing all these compounds from known starting materials are provided.

28 Claims, No Drawings

PIPERAZINYL-SUBSTITUTED PYRIDINE AND IMIDAZOLE ANTI-ARRHYTHMIC AGENTS

BACKGROUND OF THE INVENTION

This invention relates to certain piperazinyl-pyridines and piperazinyl-imidazoles which are antiarrhythmic agents, and to intermediates therefor.

The compounds of the invention prolong the duration of the action potential in cardiac muscle and conducting tissue, and thereby increase refractories to premature stimuli. Thus, they are Class III antiarrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrythmias including atrial and ventricular fibrillation. Because they do not alter the speed at which impulses are conducted, they have less propensity than current drugs (mostly Class I) to precipitate or aggravate arrhythmias, and also produce less neurological side effects. Some of the compounds also have some positive inotropic activity and therefore are particularly beneficial in patients with impaired cardiac pump function.

SUMMARY OF THE INVENTION

Thus the invention provides piperazine derivatives of the formula:

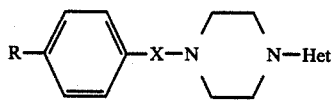

(I)

and their pharmaceutically acceptable salts, wherein "Het" is selected from (a) a 3- or 4-pyridinyl group optionally substituted by one or two substituents each independently selected from $C_1$–$C_4$ alkyl and amino, (b) a 2-pyridinyl group substituted by an amino group, (c) a 2-imidazolyl group optionally substituted by one or two $C_1$–$C_4$ alkyl groups and (d) a 2-, 3- or 4-pyridinyl group substituted by a nitro group, or an N-oxide thereof, or a 2-, 3- or 4-pyridinyl group substituted by a group of the formula —NHCOO($C_1$–$C_4$ alkyl);

R is selected from (a) —NHSO$_2$R$^3$ where R$^3$ is $C_1$–$C_4$ alkyl, $C_3$–$C_7$ cycloalkyl or —NR$^1$R$^2$ where R$^1$ and R$^2$ are each independently H or $C_1$–$C_4$ alkyl, (b) —SO$_2$NR$^1$R$^2$ where R$^1$ and R$^2$ are as defined above, (c) nitro, (d) amino and (e) acetamido;

and X is a group of the formula —(CH$_2$)$_m$— where m is an integer of from 1 to 4, —CO(CH$_2$)$_n$— or —CH(OH)(CH$_2$)$_n$— where n is 1, 2 or 3.

The compounds of the formula (I) in which R is nitro, amino or acetamido are synthetic intermediates in addition to being antiarrhythmic agents.

The compounds of the formula (I) in which "Het" is as defined in sub-section (d) above are useful as synthetic intermediates only.

One preferred group of compounds of the formula (I) are those wherein

"Het" is a 3- or 4-pyridinyl group optionally substituted by 1 or 2 substituents each independently selected from $C_1$–$C_4$ alkyl and amino;

R is selected from (a) —NHSO$_2$R$^3$ where R$^3$ is $C_1$–$C_4$ alkyl, $C_3$–$C_7$ cycloalkyl, or —NR$^1$R$^2$ where R$^1$ and R$^2$ are each independently H or $C_1$–$C_4$ alkyl, (b) —SO$_2$NR$^1$R$^2$ where R$^1$ and R$^2$ are as defined above, (c) nitro and (d) amino; and X is a grop of the formula —(CH$_2$)$_m$— where m is an integer of from 1 to 4; —CO(CH$_2$)$_n$— or —CH(OH)(CH$_2$)$_n$— where n is 1, 2 or 3.

In an alternative aspect, "Het" is preferably selected from (a) a 3- or 4-pyridinyl group optionally substituted by an amino or methyl group (b) a 2-pyridinyl group substituted by an amino group, (c) a 2-imidazolyl group substituted by a methyl group, (d) a 2-, 3- or 4-pyridinyl group substituted by a nitro group, or an N-oxide thereof, or a 2-, 3- or 4-pyridinyl group substituted by a group of the formula —NHCOO($C_1$–$C_4$ alkyl) [preferably —NHCOOC$_2$H$_5$].

R is preferably selected from (a) —NHSO$_2$R$^3$ where R$^3$ is $C_1$–$C_4$ alkyl or —N($C_1$–$C_4$ alkyl)$_2$, (b) —SO$_2$NHR$^1$ where R$^1$ is H or $C_1$–$C_4$ alkyl, (c) nitro, (d) amino and (e) acetamido.

X is preferably —CH$_2$—, —(CH$_2$)$_2$—, —COCH$_2$—, —CO(CH$_2$)$_2$—, —CH(OH)CH$_2$— or —CH(OH)(CH$_2$)$_2$—.

Specific Examples of R are —NHSO$_2$CH$_3$, —NHSO$_2$C$_2$H$_5$, —NHSO$_2$N(CH$_3$)$_2$, —SO$_2$NH$_2$, —SO$_2$NHCH$_3$, —NO$_2$, —NH$_2$ and —NHCOCH$_3$.

Specific Examples of "Het" are 3-pyridinyl, 4-amino-3-pyridinyl, 4-nitro-1-oxido-3-pyridinyl, 4-pyridinyl, 2-methyl-4-pyridinyl, 3-methyl-4-pyridinyl, 2-amino-4-pyridinyl, 2-ethoxycarbonylamino-4-pyridinyl, 4-nitro-2-pyridinyl, 4-amino-2-pyridinyl and 1-methyl-imidazol-2-yl.

"Het" is preferably 4-pyridinyl, 2-amino-4-pyridinyl or 4-amino-2-pyridinyl. X is preferably —COCH$_2$— or —CH(OH)CH$_2$—. R is preferably —NHSO$_2$CH$_3$, —SO$_2$NH$_2$ or —SO$_2$NHCH$_3$.

"Het" is most preferably 4-pyridinyl. X is most preferably —COCH$_2$— or —CH(OH)CH$_2$—. R is most preferably —NHSO$_2$CH$_3$.

Accordingly, one group of compounds of the present invention of particular medicinal interest is that of the formula:

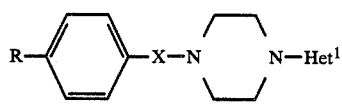

(IA)

and their pharmaceutically acceptable salts, wherein "Het$^1$" is selected from (a) 3- or 4-pyridinyl group optionally substituted by one or two substituents each independently selected from $C_1$–$C_4$ alkyl and amino, (b) a 2-pyridinyl group substituted by a amino group and (c) a 2-imidazolyl group optionally substituted by one or two $C_1$–$C_4$ alkyl groups; R is selected from (a) —NHSO$_2$R$^3$ where R$^3$ is $C_1$–$C_4$ alkyl, $C_3$–$C_7$ cycloalkyl or —NR$^1$R$^2$ wherein R$^1$ and R$^2$ are each independently hydrogen or $C_1$–$C_4$ alkyl, (b) —SO$_2$NR$^1$R$^2$ where R$^1$ and R$^2$ are each independently hydrogen or $C_1$–$C_4$ alkyl, (c) nitro, (d) amino and (e) acetamido; and X is a group of the formula —(CH$_2$)$_m$— where m is an integer of from one to four, inclusive, or it is —CO(CH$_2$)$_n$— or —CH(OH)(CH$_2$)$_n$— where n is one, two or three. Preferred compounds within this group include those where "Het$^1$" is selected from (a) 3- or 4-pyridinyl group optionally substituted by an amino or methyl group, (b) a 2-pyridinyl group substituted by an amino group and (c) a 2-imidazolyl group substituted by a methyl group; R is selected from (a) —NHSO$_2$R$^3$ where R$^3$ is C$_1$-C$_4$ alkyl or —N(C$_1$-C$_4$ alkyl)$_2$, (b) —SO$_2$NHR$^1$ where R$^1$ is hydrogen or C$_1$-C$_4$ alkyl, (c) nitro, (d) amino and (e) acetamido; and X is —CH$_2$, —(CH$_2$)$_2$—, —COCH$_2$—, —CO(CH$_2$)$_2$—, —CH(OH)CH$_2$— or —CH(OH)(CH$_2$)$_2$—. A particularly preferred group of compounds within this category are those where "Het$^1$" is 3-pyridinyl, 4-amino-3-pyrdinyl, 4-pyridinyl, 2-methyl-4-pyridinyl, 3-methyl-4-pyridinyl, 2-amino-4-pyridinyl, 4-amino-2-pyridinyl or 1-methylimidazol-2-yl; R is —NHSO$_2$CH$_3$, —NHSO$_2$C$_2$H$_5$, —NHSO$_2$N—(CH$_3$)$_2$, —SO$_2$NH$_2$, —SO$_2$NHCH$_3$, —NO$_2$, —NH$_2$ or —NHCOCH$_3$; and X is —COCH$_2$— or —CH(OH)CH$_2$—. Most preferably, "Het$^1$" is 4-pyridinyl, 2-amino-4-pyridinyl or 4-amino-2-pyridinyl, and R is —NHSO$_2$CH$_3$, —SO$_2$NH$_2$ or —SO$_2$NHCH$_3$.

Another group of compounds of the present invention of particular medicinal interest is that of structural formula (IA), as hereinbefore set forth, and their pharmaceutically acceptable salts, wherein "Het$^1$" is a 3- or 4-pyridinyl group optionally substituted by one or two substituents each independently selected from C$_1$-C$_4$ alkyl and amino; R is selected from (a) —NHSO$_2$R$^3$ where R$^3$ is C$_1$-C$_4$ alkyl, C$_3$-C$_7$ cycloalkyl or —NR$^1$R$^2$ wherein R$^1$ and R$^2$ are each independently hydrogen or C$_1$-C$_4$ alkyl, (c) nitro and (d) amino; and X is a group of the formula —(CH$_2$)$_m$— where m is an integer of from one to four, inclusive, or it is —CO(CH$_2$)$_n$— or —CH(OH)(CH$_2$)$_n$— where n is one, two or three. Preferred compounds within this group include those where "Het$^1$" is 4-pyridinyl or 2-amino-4-pyridinyl; R is —NHSO$_2$CH$_3$, —NHSO$_2$C$_2$H$_5$, —NHSO$_2$N(CH$_3$)$_2$, —SO$_2$NH$_2$, —SO$_2$NHCH$_3$, NO$_2$ or NH$_2$; and X is —CH$_2$—, (CH$_2$)$_2$—, —COCH$_2$—, —CO(CH$_2$)$_2$—, —CH(OH)CH$_2$— or —CH(OH)— —(CH$_2$)$_2$—. A particularly preferred group of compounds within this category are those where "Het$^1$" is defined as aforesaid; and R is —NHSO$_2$CH$_3$, —SO$_2$NH$_2$ or —SO$_2$NHCH$_3$, and X is —COCH$_2$— or —CH(OH)CH$_2$—.

There is also included within the purview of this invention novel intermediates, which are piperazinyl-substituted pyridine compounds of the formula:

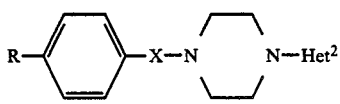

(IB)

wherein "Het$^2$" is a 2-, 3- or 4-pyridinyl group substituted by a nitro group, or an N-oxide derivative thereof, or a 2-, 3- or 4-pyridinyl group substituted by a group of the formula —NHCOO(C$_1$-C$_4$ alkyl); R is selected from (a) —NHSO$_2$R$^3$ where R$^3$ is C$_1$-C$_4$ alkyl, C$_3$-C$_7$ cycloalkyl or —NR$^1$R$^2$ wherein R$^1$ and R$^2$ are each independently hydrogen or C$_1$-C$_4$ alkyl, (b) —SO$_2$NR$^1$R$^2$ where R$^1$ and R$^2$ are each independently hydrogen or C$_1$-C$_4$ alkyl, (c) nitro, (d) amino and (e) acetamido; and X is a group of the formula —(CH$_2$)$_m$— where m is an integer of from one to four, inclusive, or it is —CO(CH$_2$)$_n$— or —CH(OH)(CH$_2$)$_n$— where n is one, two or three. Preferred compounds within this category include those of the above formula wherein "Het$^2$" is 4-nitro-1-oxide-3-pyridinyl, 2-ethoxycarbonylamino-4-pyridinyl or 4-nitro-2-pyridinyl.

Additionally, the invention also includes within its scope further intermediates, which are 4-substituted piperazine compounds of the formula:

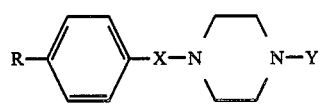

(VI) and (VII)

wherein R is selected from (a) —NHSO$_2$R$^3$ where R$^3$ is C$_1$-C$_4$ alkyl, C$_3$-C$_7$ cycloalkyl or —NR$^1$R$^2$ wherein R$^1$ and R$^2$ are each independently hydrogen or C$_1$-C$_4$ alkyl, (b) —SO$_2$NR$^1$R$^2$ where R$^1$ and R$^2$ are each independently hydrogen or C$_1$-C$_4$ alkyl, (c) nitro, (d) amino and (e) acetamido; X is a group of the formula —(CH$_2$)$_m$— where m is an integer of from one to four, inclusive, or it is —CO(CH$_2$)$_n$— or —CH(OH)(CH$_2$)$_n$— where n is one, two or three; and Y is hydrogen or an amino-protecting group. Preferred compounds within this category include those of the above formula wherein the amino-protecting group is acetyl, formyl or benzyl.

The most preferred medicinal compound of formula (I) or (IA) is actually N-{4-[1-hydroxy-2-(4-[4-pyridinyl]-1-piperazinyl)ethyl]phenyl}-methanesulphonamide where "Het" or "Het$^1$" is 4-pyridinyl, R is —NHSO$_2$CH$_3$ and X is —CH(OH)CH$_2$—. [In formula (I), it is to be understood that "Het" encompasses the definitions of both "Het$^1$" of formula (IA) and "Het$^2$" of formula (IB).]

The most preferred compound of the formula (I) has the formula:

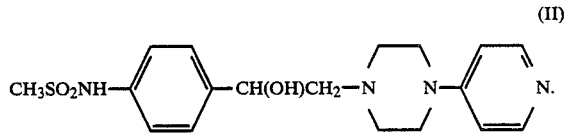

(II)

Where the compounds of the formula (I) have an optically active centre, then the invention includes both the resolved and unresolved forms.

The pharmaceutically acceptable salts of the compounds of the formula (I) include acid addition salts formed from acids which form non-toxic acid addition salts containing pharmaceutically acceptable anions, such as hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, besylate and p-toluenesulphonate salts. Some of the compounds, e.g. those in which R$^3$ is alkyl or cycloalkyl, may also form metal salts, particularly alkaline earth and alkali metal salts. The preferred metal salts are the sodium and potassium salts. All the salts are preparable by conventional techniques.

For assessment of effects of the compounds on atrial refractoriness, guinea pig right hemiatria are mounted in a bath containing physiological salt solution, and one end is connected to a force transducer. Tissues are stimulated at 1 Hz using field electrodes. Effective refractory period (ERP) is measured by introducing premature stimuli (S$_2$) after every 8th basic stimulus (S$_1$). The S$_1$S$_2$ coupling interval is gradually increased until S$_2$ reproducibly elicits a propagated response. This is defined as the ERP. The concentration of compound required to increase ERP by 25% (ED$_{25}$) is then determined. ERP is also measured in guinea pig right papillary muscles incubated in physiological salt solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and vetricular ERP's are also measured in anaesthetised or conscious dogs by the extrastimulus technique whilst the atrium or right ventricle is being paced at a constant rate.

The antiarrhythmic compounds of the formula (I) can be administered alone but will generally be administered in admixture with a pharmaceutical carrier selected with regard to the intended route of administration and standard pharmaceutical practice. They can be administered both to patients suffering from arrythmias and also prophylactically to those likely to develop arrhythmias. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as ventricular and supraventricular arrythmias, including atrial and ventricular fibrillation, it is expected that oral dosages of the antiarrhythmic compounds of the formula (I) will be in the range from 1 to 75 mg daily, taken in up to 4 divided doses per day, for an average adult patient (70 kg). Dosages for intravenous administration would be expected to be within the range 0.5 to 10 mg per single dose as required. A severe cardiac arrythmia is preferably treated by the i.v. route in order to effect a rapid conversion to the normal rhythm. Thus for a typical adult patient, individual tablets or capsules might contain 1 to 25 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising an antiarrhythmic compound of the formula (I) as defined above or pharmaceutically acceptable salt thereof, together with a pharmaceutically acceptable diluent or carrier.

The invention also provides a method of preventing or reducing cardiac arrythmias in a human being, which comprises administering to said human an effective amount of an antiarrhythmic compound of the formula (I) or pharmaceutically acceptable salt thereof, or of a pharmaceutical composition as defined above.

The invention yet further provides an antiarrhythmic compound of the formula (I), or a pharmaceutically acceptable salt thereof, for use as a medicament.

The invention also provides the use of an antiarrhythmic compound of the formula (I), or a pharmaceutically acceptable salt thereof for the manufacture of a medicament for the prevention or reduction of cardiac arrhythmias.

DETAILED DESCRIPTION OF THE INVENTION

The compounds of the formula (I) can be prepared by the following routes:

(1) This route can be illustrated schematically as follows:

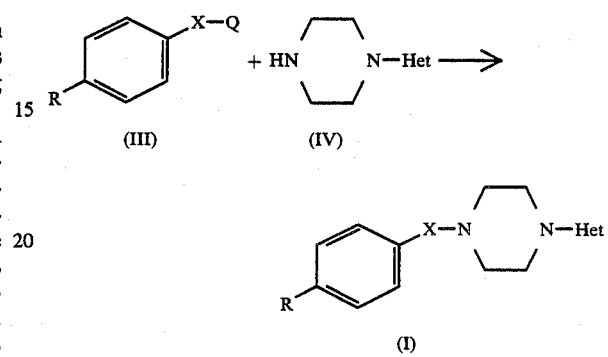

R, X and Het are as defined for formula (I) and Q is a leaving group such as Br, Cl, $-OSO_2(C_1-C_4$ alkyl) or $-OSO_2$phenyl (the phenyl group can be optionally substituted, e.g. by $C_1-C_4$ alkyl, preferably methyl). Q is preferably Br or $-OSO_2CH_3$. Q is most preferably Br.

The reaction is typically carried out in a suitable organic solvent, e.g. methanol, ethanol or N,N-dimethylformamide, and at a temperature of from room temperature (about 20° C.) up to the reflux temperature of the reaction mixture, and preferably in the range of from 20°–100° C. The presence of an additional base (acid acceptor) such as triethylamine or sodium bicarbonate is desirable. After the reaction is complete, the product can be isolated and purified by conventional procedures.

The starting materials of the formulae (III) and (IV) are either known compounds or can be prepared conventionally, e.g. as follows:

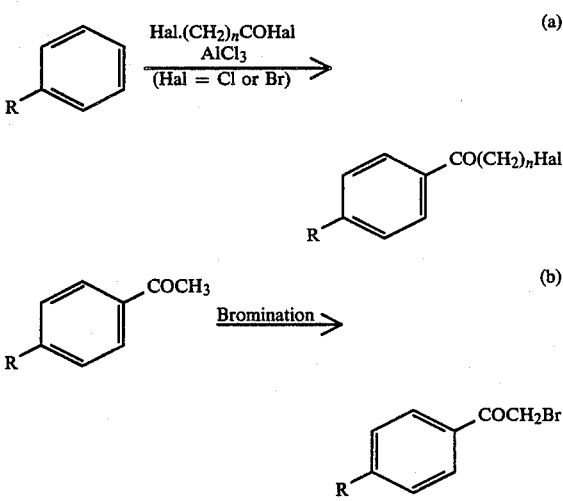

The bromination can be carried out conventionally, e.g. using $Br_2/CHCl_3$/benzoyl peroxide (or other free radical initiator), $Br_2$/dioxan/ether, or pyridinium perbromide/acetic acid.

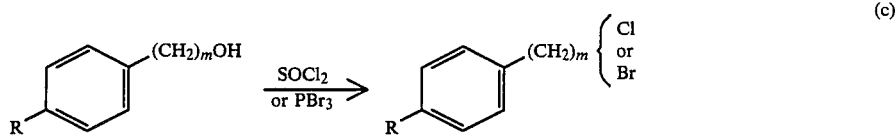
(c)
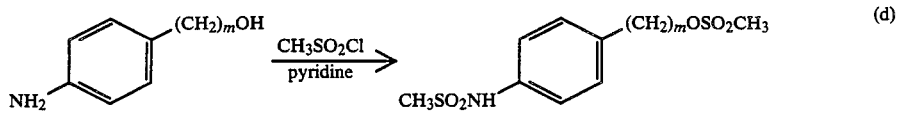
(d)
when R is non amino:
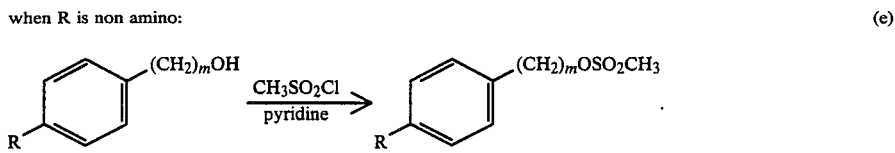
(e)
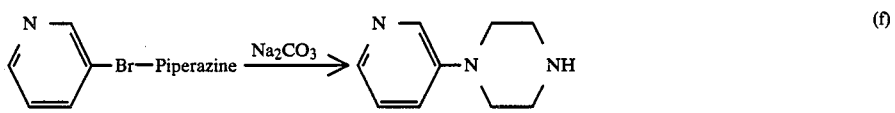
(f)
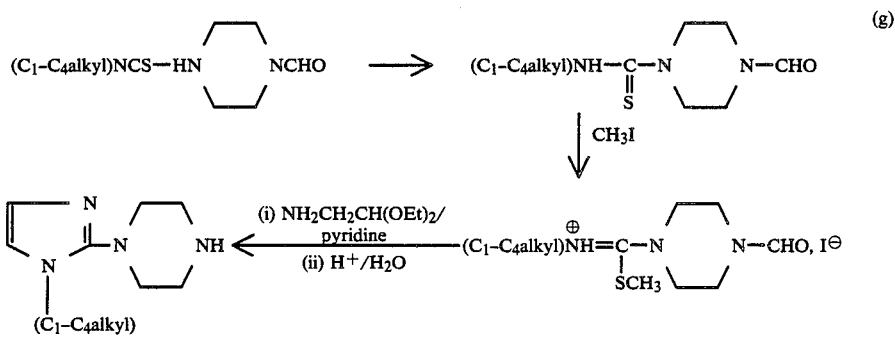
(g)
Other imidazoles can be prepared similarly using HSCN or an acetal substituted by alkyl on the appropriate carbon atoms.
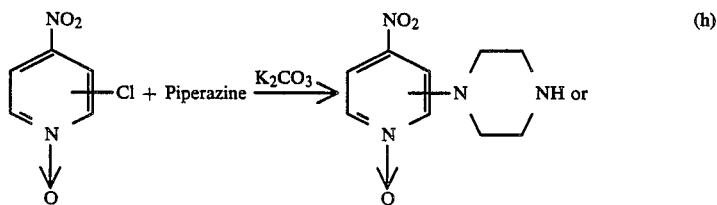
(h)
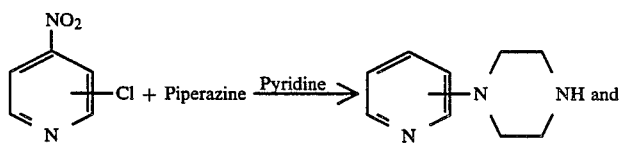
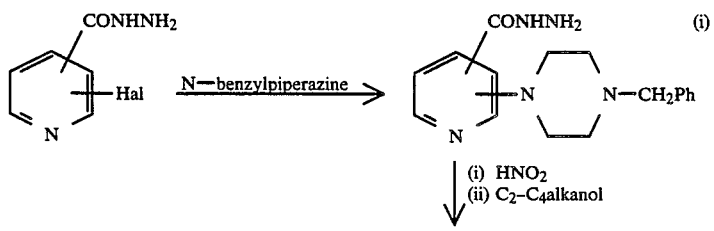
(i)

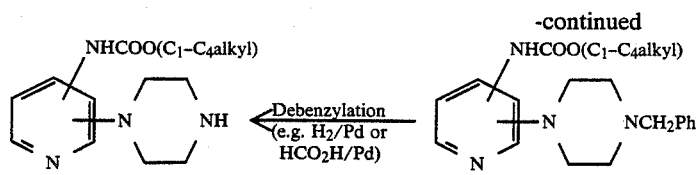

Starting materials of the formula (III) having X as —CH(OH)(CH$_2$)$_n$— can be prepared by the conventional reduction of the ketones in which X is —CO(CH$_2$)$_n$—, e.g. using NaBH$_4$ or H$_2$/Pd/C. Use of NaBH$_4$ is preferred if reduction of nitro to amino needs to be avoided.

(2) This is related to route (1) above and is illustrated schematically as follows:

dimethylformamide, at up to the reflux temperature, and again preferably in the presence of an additional base such as sodium bicarbonate.

To obtain end-products in which X is —CH(OH)(CH$_2$)$_n$—, it is often convenient to start with a compound of the formula (III) in which X is —CO(CH$_2$)$_n$—, and reduce this, e.g. with NaBH$_4$/H$_2$O before deprotection. When Z is acetyl or formyl, depro-

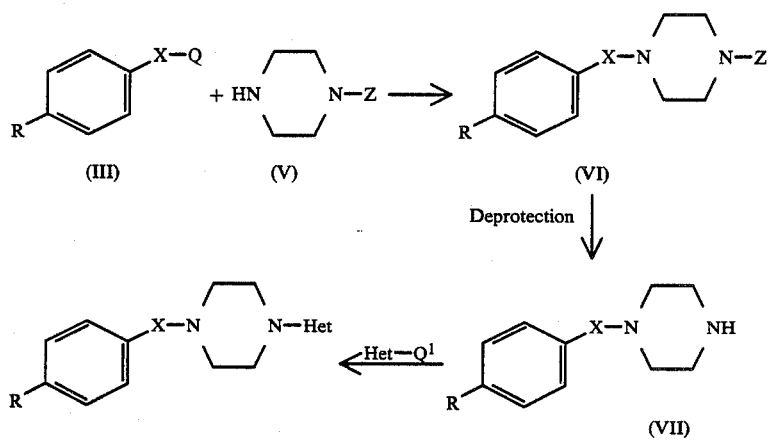

The intermediates of the formula (VI) and (VII) also form a part of the invention.

In the above, R, X and "Het" are as defined for formula (I), Q is a leaving group [see route (1)], Q$^1$ is a leaving group (preferably Cl, Br or I), and Z is an amino-protecting group, e.g. benzyl, acetyl or formyl.

The first step is carried out under similar conditions to those described for route (1). The subsequent deprotection can be carried out conventionally, e.g. by using H$_2$/Pd/C when Z is benzyl, or by hydrolysis (e.g. using aqueous HCl at reflux) when Z is acetyl or formyl.

The final stage, i.e. the reaction of the piperazine with the substituted heterocycle, can also be carried out conventionally, typically by carrying out the reaction in a suitable organic solvent, e.g. amyl alcohol or N,N- tection is simply carried out by acidifying the solution containing the reduced intermediate.

(3) Compounds in which X is —CH(OH)(CH$_2$)$_n$— are most conveniently prepared by the reduction of the corresponding ketones in which X is —CO(CH$_2$)$_n$—, preferred reducing agents being NaBH$_4$ or H$_2$/Pd/C. The reaction conditions are conventional. For example, the reaction with sodium borohydride is typically preferably carried out in ethanol with heating at up to the reflux temperature. Sodium borohydride is recommended when reduction of a nitro substituent is not required.

(4) Some of the compounds of the formula (I) can also be prepared from the corresponding compounds having R as —NH$_2$, e.g. as follows:

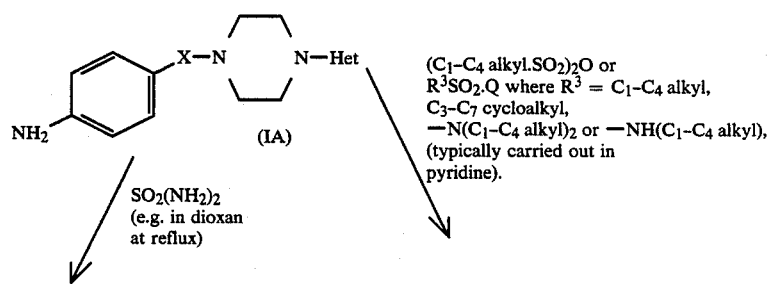

-continued

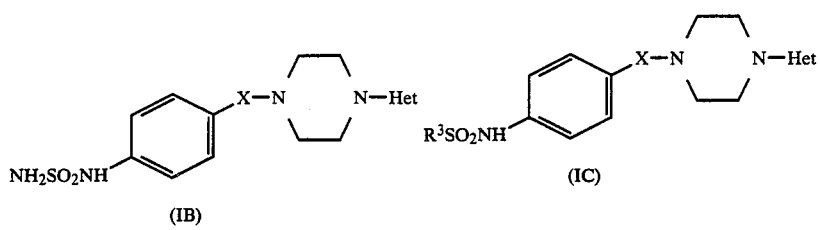

X and Het are as defined for formula (I), and Q is a leaving group, preferably Cl.

The compounds of the formula (IA) are conveniently available as follows:

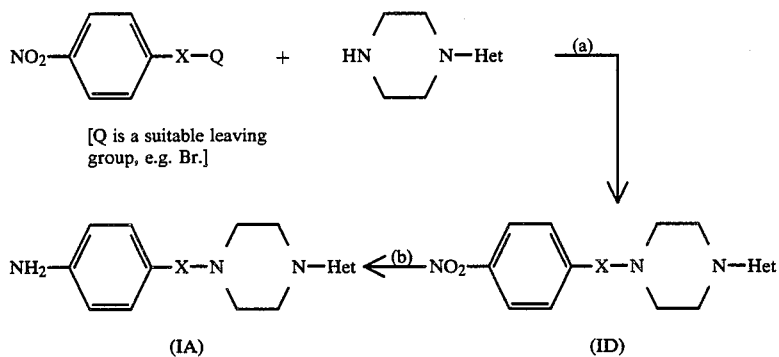

Step (a) is preferably carried in the presence of a base (e.g. NaHCO₃); and step (b) is carried out by reduction, typically using H₂/Pd/C, or by chemical means, e.g. metal/acid.

The aminophenyl compounds of the formula (IA) can also be prepared by the hydrolysis of the corresponding acetamidophenyl derivatives using, e.g., aqueous hydrochloric acid with heating.

(5) This route is similar to route (1) above but only produces compounds in which X is —CH(OH)CH₂—, and is illustrated as follows:

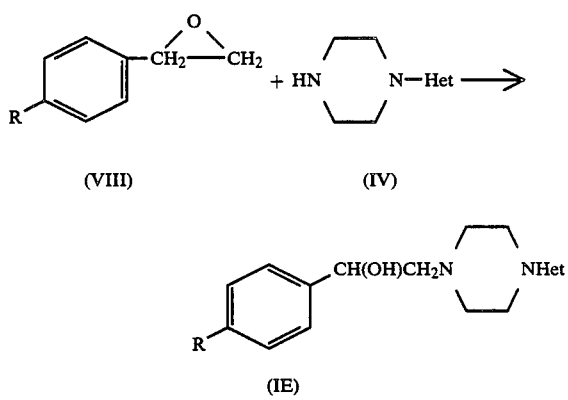

The reaction can again be carried out in a conventional manner, typically in an organic solvent, e.g. ethanol, at up to the reflux temperature of the reaction mixture. After reaction, the product can be isolated and purified conventionally.

In a modification of this route, the styrene oxide (VIII) can be reacted with an N-protected piperazine of the formula (V) (see route 2), with the subsequent steps then as for route (2).

(6) The compounds of the formula (I) in which "Het" is an amino-substituted 2-, 3- or 4-pyridinyl group can also be prepared by the reduction of the corresponding nitropyridinyl compounds, e.g. by catalytic hydogenation, e.g. using H₂/Pd/C. The corresponding nitropyridinyl N-oxides can also be reduced to the corresponding aminopyridinyl derivatives, typically by catalytic hydrogenation using e.g. H₂/Raney nickel.

Hydrolysis (acid or alkaline) of the corresponding $C_1$-$C_4$ alkoxycarbonylaminopyridinyl derivatives, themselves available conventionally, can also be used to prepare the aminopyridinyl compounds. and (7) The compounds of the formula (I) in which X is —CO(CH₂)₂— can also be prepared by the Mannich reaction by the reaction of a compound of the formula (IV) with formaldehyde and a compound of the formula:

$$R\!-\!\!\!\bigcirc\!\!\!-\!COCH_3 \quad (IX)$$

The reaction is carried out conventionally. The formaldehyde is typically generated by the decomposition of paraformaldehyde. Thus the reaction is typically carried out by heating the reactants at up to the reflux temperature under acidic conditions in a suitable organic solvent, e.g. ethanol. The product can be recovered and isolated by conventional techniques.

The salts of the compounds of the formula (I) are also available conventionally.

The following Examples illustrate the invention:

EXAMPLE 1

N-{4-[2-(4-[4-Pyridinyl]-1-piperazinyl)acetyl]phenyl} methanesulphonamide

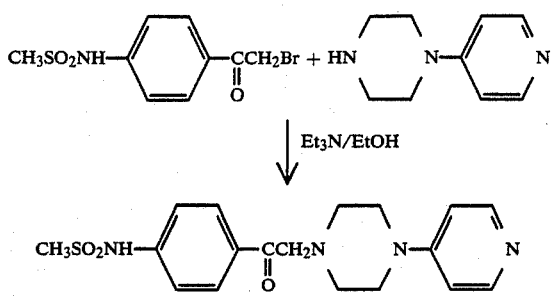

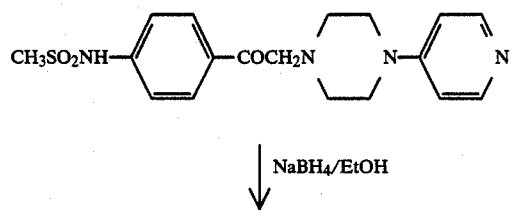

A mixture of 1-(4-pyridinyl)piperazine (3.50 g), N-[4-bromoacetylphenyl]methanesulphonamide (5.74 g) (see procedure 2 of J. Med. Chem., 9, 94, 1966), triethylamine (6 ml) and ethanol (60 ml) was stirred at room temperature for 18 hours. The solid was filtered off, washed with ethanol, dried and chromatographed on silica gel. Elution was commenced with dichloromethane, gradually increasing the eluent polarity by the addition of methanol, finally using $CH_2Cl_2$/MeOH (4:1). The later fractions were combined and evaporated to give the title compound as a solid (4.50 g), m.p. 227°–233° C. with decomposition (from ethanol).

Analysis %: Found: C, 57.86; H, 6.00; N, 14.75; $C_{18}H_{22}N_4O_3S$ requires: C, 57.73; H, 5.92; N, 14.96.

EXAMPLE 2

N-{4-[1-Hydroxy-2-(4-[4-pyridinyl]-1-piperazinyl)ethyl]phenyl}methanesulphonamide

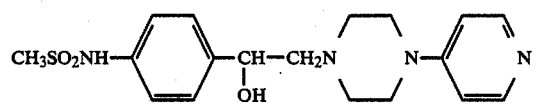

Sodium borohydride (25 mg) was added to a solution of N-{4-[2-(4-pyridinyl)-1-piperazinyl)acetyl]phenyl} methanesulphonamide (200 mg—see Example 1) in ethanol (30 ml) at reflux. The solution was heated under reflux for 3 hours and further 25 mg. quantities of sodium borohydride were added after 1 and 2 hours. The solution was then evaporated and the residue was dissolved in water. 5N Hydrochloric acid was added until the solution was just acidic and then the pH was adjusted to 7–8 by the addition of sodium bicarbonate. The solution was extracted several times with ethyl acetate and the combined extracts were evaporated. The residue was crystallised from methanol/$H_2O$ to give the title compound (118 mg), m.p. 214°–6° C., with decomposition.

Analysis %: Found: C, 57.17; H, 6.53; N, 14.83. $C_{18}H_{24}N_4O_3S$ requires: C, 57.42; H, 6.43; N, 14.88.

EXAMPLE 3

N-{4-[2-(4-[4-pyridinyl]-1-piperazinyl)ethyl]phenyl} methanesulphonamide (i) N-[4-(2-{methylsulphonyloxy}ethyl)phenyl]methane sulphonamide

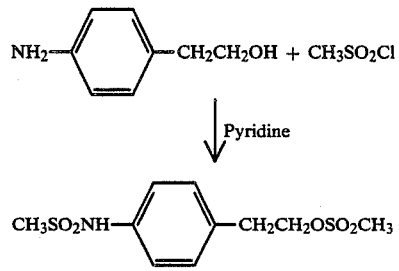

Methanesulphonyl chloride (50.4 g) was added dropwise to a stirred solution of 2-(4-aminophenyl)-ethanol (27.44 g) in dry pyridine (300 ml) at 0° C. The solution was stirred at 0° C. for 30 minutes and then at room temperature for 2.5 hours. It was then poured into water and the solid was filtered off, washed with water, dried and crystallised from ethyl acetate to give the title compound (39.0 g), m.p. 136°–137° C.

Analysis %: Found: C, 40.59; H, 5.22; N, 4.93; $C_{10}H_{15}NO_5S_2$ requires: C, 40.94; H, 5.15; N, 4.76.

(ii) N-{4-[2-(4-[4-Pyridinyl]-1-piperazinyl)ethyl]-phenyl}methanesulphonamide

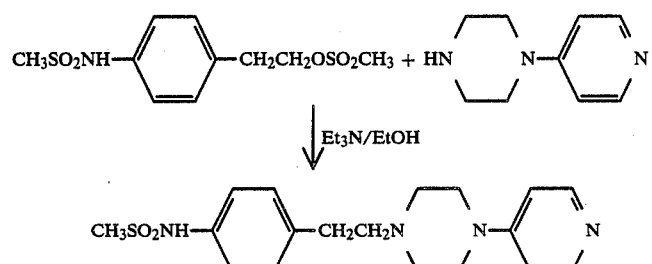

A solution of 1-(4-pyridinyl)piperazine (1.63 g), N-[4-(2-methylsulphonyloxyethyl)phenyl]methanesulphonamide (2.93 g) and triethylamine (1.01 g) in ethanol (25 ml) was heated under reflux for 18 hours and then evaporated. The resulting oil was partitioned between dichloromethane and water (some insoluble material remained in the aqueous layer). The aqueous layer was washed with dichloromethane and the organic layers were combined, washed with water and dried ($Na_2SO_4$). Evaporation of the solvent gave an oil which was chromatographed in silica gel. Elution with dichloromethane/methanol (19:1) first gave some impurity followed by a solid which was crystallised from methanol/ethyl acetate to give the title compound (0.75 g), m.p. 208°–210° C.

Analysis %: Found: C, 60.22; H, 6.86; N, 15.17; $C_{18}H_{24}N_4O_2S$ requires: C, 59.97; H, 6.71; N, 15.54.

EXAMPLE 4

1-(4-Pyridinyl)-4-{2-[4-nitrophenyl]-2-hydroxyethyl}piperazine

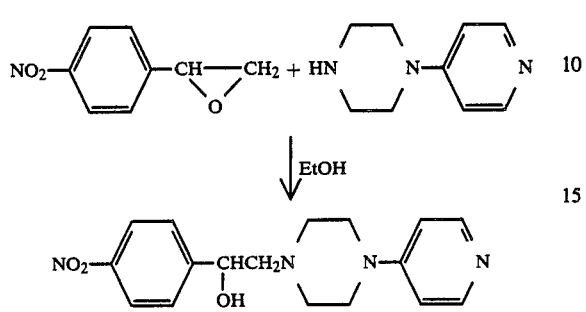

A solution of 1-(4-pyridinyl)piperazine (0.247 g) and 4-nitrostyrene oxide (0.25 g) in ethanol (5 ml) was heated under reflux for 1 hour and then evaporated. The residue was dissolved in dichloromethane and the solution was extracted with 2N hydrochloric acid. The acidic extract was made basic (pH 8-9) with sodium bicarbonate and the mixture was extracted several times with dichloromethane. The combined extracts were dried ($Na_2SO_4$) and evaporated to give an oil which was chromatographed on silica gel. Elution was commenced with dichloromethane, gradually increasing the polarity to $CH_2Cl_2$/MeOH (9:1). Some impurity was eluted first followed by pure product. The product-containing fractions were combined and evaporated to give the title compound as a solid (0.13 g), m.p. 166°-167° C. (from dichloromethane).

Analysis %: Found: C, 61.96; H, 6.23; N, 17.08; $C_{17}H_{20}N_4O_3$ requires: C, 62.18; H, 6.14; N, 17.06.

EXAMPLE 5

1-(4-Pyridinyl)-4-(4-nitrobenzyl)piperazine

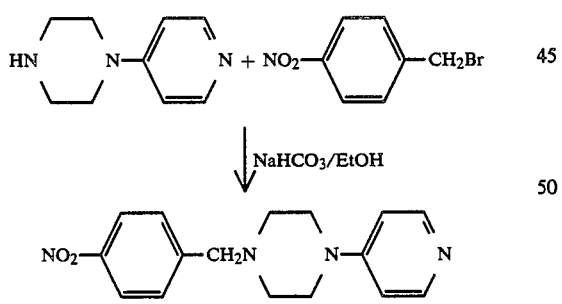

A mixture of 1-(4-pyridinyl)piperazine (1.0 g), 4-nitrobenzyl bromide (1.32 g), sodium bicarbonate (3.0 g) and ethanol (15 ml) was heated under reflux with stirring for 5 hours and then cooled and filtered. The filtrate was evaporated and the residue was dissolved in dichloromethane. The solution was washed with water, dried ($Na_2SO_4$) and evaporated. The residue was chromatographed on silica gel using dichloromethane/methanol (97:3) as eluent. After elution of some impurity, the product was eluted as an oil which crystallised on standing. The solid was crystallised from ethyl acetate/hexane to give the title compound (0.57 g), m.p. 119°-121° C.

Analysis %: Found: C, 64.30; H, 6.08; N, 18.39; $C_{16}H_{18}N_4O_2$ requires: C, 64.41; H, 6.08; N, 18.78.

EXAMPLE 6

1-(4-Pyridinyl)-4-(4-aminobenzyl)piperazine

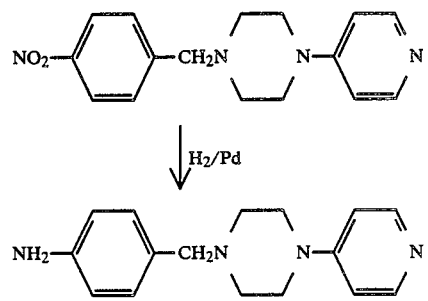

A mixture of 1-(4-pyridinyl)-4-(4-nitrobenzyl)-piperazine (0.63 g—see Example 5) and 5% palladium on carbon (0.1 g) in ethanol (20 ml) was hydrogenated at 50° C. and 3 atmospheres (20.68 kPa) pressure until reduction was complete. The catalyst was filtered off and the solution was evaporated. The residue was chromatographed on silica gel using dichloromethane/methanol (50:1) as eluent. The product-containing fractions were combined and evaporated and the residue was crystallised from methanol/ethyl acetate to give the title compound, (0.20 g), m.p. 222°-224° C.

Analysis %: Found: C, 71.24; H, 7.66; N, 21.11; $C_{16}H_{20}N_4$ requires: C, 71.61; H, 7.51; N, 20.88.

EXAMPLE 7

N-{4-[4-(4-Pyridinyl)-1-piperazinylmethyl]phenyl}-methanesulphonamide

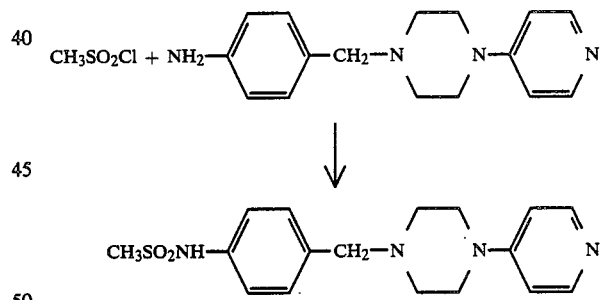

Methanesulphonyl chloride (52 mg) was added to a stirred mixture of 1-(4-pyridinyl)-4-(4-aminobenzyl)-piperazine (110 mg—see Example 6) in dry pyridine (3 ml) and stirring was continued for 2 hours. The solution was evaporated and the residue was dissolved in water. Addition of sodium bicarbonate solution gave a solid. The mixture was extracted several times with ethyl acetate and the combined extracts were dried ($Na_2SO_4$) and evaporated. The residue was crystallised from methanol/ethyl acetate to give the title compound (75 mg), m.p. 193°-195° C.

Analysis %: Found: C, 58.78; H, 6.50; N, 15.96; $C_{17}H_{22}N_4O_2S$ requires: C, 58.93; H, 6.40; N, 16.17.

EXAMPLE 8

N-Methyl-4-{2-[4-(4-pyridinyl)-1-piperazinyl]acetyl}benzenesulphonamide

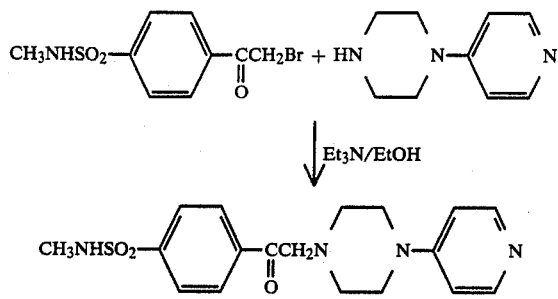

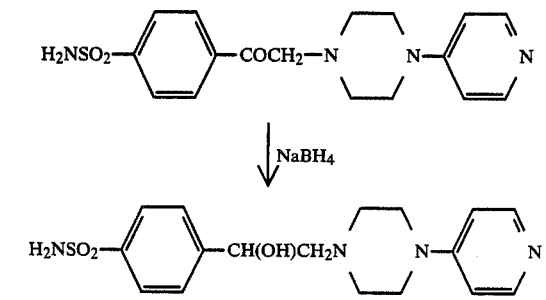

Analysis %: Found: C, 56.80; H, 5.80; N, 15.31; $C_{17}H_{20}N_4O_3S$ requires: C, 56.65; H, 5.59; N, 15.55.

EXAMPLE 11

4-{1-Hydroxy-2-[4-(4-pyridinyl)-1-piperazinyl]ethyl}benzenesulphonamide

Treatment of 1-(4-pyridinyl)piperazine (0.56 g) with N-methyl-4-bromoacetylbenzenesulphonamide (1.00 g) [see U.S. Pat. No. 2,726,264] by the method of Example 1 gave the title compound as the hemihydrate, (0.30 g), m.p. 174°–176° C.

Analysis %: Found: C, 56.63; H, 5.96; N, 14.49; $C_{18}H_{22}N_4O_3S.\tfrac{1}{2}H_2O$ requires: C, 56.38; H, 6.05; N, 14.61.

EXAMPLE 9

N-Methyl-4-{1-hydroxy-2-[4-(4-pyridinyl)-1-piperazinyl]ethyl}benzenesulphonamide

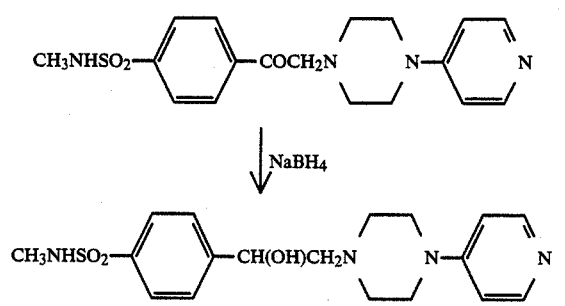

Reduction of the product of Example 10 (0.13 g) with sodium borohydride according to the method of Example 2 gave the title compound, (0.04 g), m.p. 213°–214° C.

Analysis %: Found: C, 55.61; H, 6.13; N, 15.13; $C_{17}H_{22}N_4O_3S$, $0.25H_2O$ requires: C, 55.64; H, 6.18; N, 15.27.

EXAMPLE 12

4-{2-[4-(4-Pyridinyl)-1-piperazinyl]ethyl}benzenesulphonamide (i) 4-[2-(4-Acetyl-1-piperazinyl)ethyl]benzenesulphonamide

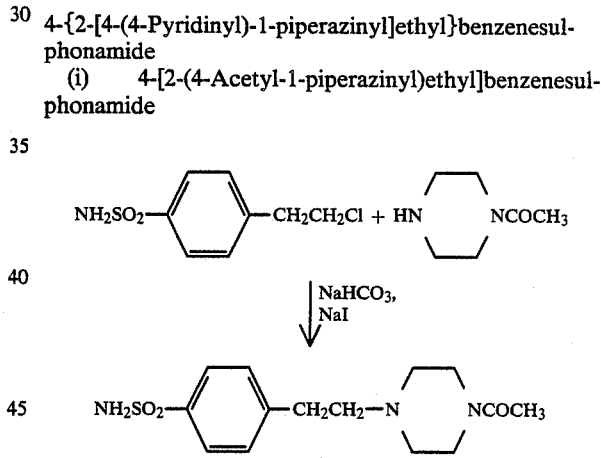

Treatment of the product of Example 8 (0.40 g) with sodium borohydride according to the method of Example 2 gave the title compound, (0.13 g), m.p. 219°–221° C.

Analysis %: Found: C, 57.15; H, 6.46; N, 14.54. $C_{18}H_{24}N_4O_3S$ requires: C, 57.42; H, 6.43; N, 14.88.

EXAMPLE 10

4-[2-{4-(4-Pyridinyl)-1-piperazinyl}acetyl]benzenesulphonamide

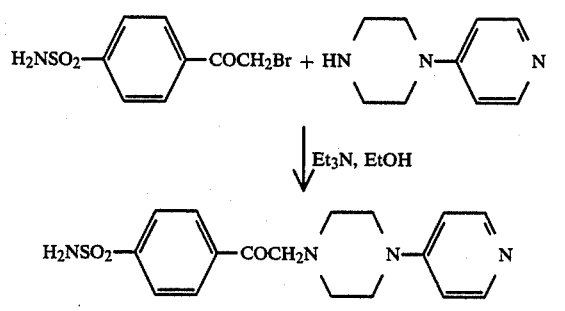

Treatment of 1-(4-pyridinyl)piperazine (0.59 g) with 4-(bromoacetyl)benzenesulphonamide (1.00 g) by the method of Example 1 gave the title compound, (0.40 g), m.p. 210°–214° C.

A mixture of 4-(2-chloroethyl)benzenesulphonamide (2.00 g), 1-acetylpiperazine (1.17 g), sodium iodide (1.37 g) and sodium bicarbonate (0.84 g) in n-butanol was heated under reflux with stirring for 66 hours. The mixture was cooled slightly and filtered. The filtrate was allowed to stand and the solid that crystallised out was filtered off and recrystallised from ethyl acetate/methanol to give the title compound (1.10 g), m.p. 203°–204.5° C.

Analysis %: Found: C, 53.86; H, 6.80; N, 13.29; $C_{14}H_{21}N_3O_3S$ requires: C, 54.00; H, 6.80; N, 13.50.

(ii) 4-[2-(1-Piperazinyl)ethyl]benzenesulphonamide

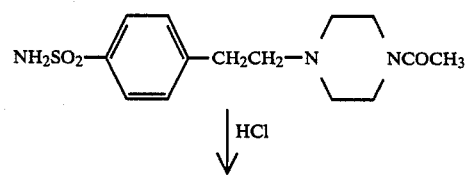

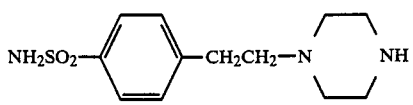

A solution of the product from part (i) (12.7 g) in 5N hydrochloric acid (250 ml) was heated under reflux for 2.5 hours and then evaporated. The residue was dissolved in water and the solution was made basic (pH 8–9) by the addition of solid sodium bicarbonate. The mixture was evaporated and the residue was extracted several times with boiling methanol. The methanol extracts were combined and evaporated and the residue was stirred with water for 15 minutes. The solid was filtered off and crystallised from methanol to give the title compound, (7.85 g), m.p. 239°–242° C.

Analysis %: Found: C, 53.25; H, 7.20; N, 15.40; $C_{12}H_{19}N_3O_2S$ requires: C, 53.50; H, 7.11; N, 15.40.

(iii) 4-{2-[4-(4-Pyridinyl)-1-piperazinyl]-ethyl}benzenesulphonamide

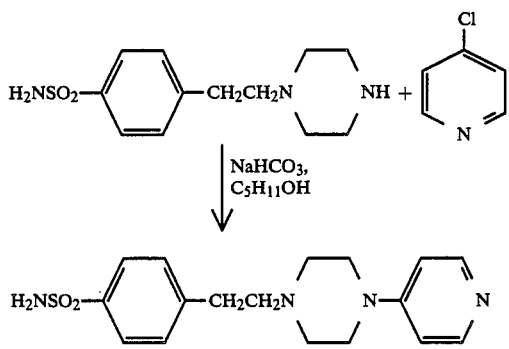

A mixture of the product from part (ii) (2.00 g) and sodium bicarbonate (1.87 g) was heated to reflux with stirring in amyl alcohol. 4-Chloropyridine hydrochloride (1.12 g) was added and heating and stirring were continued for 18 hours. The mixture was cooled, filtered and the filtrate was evaporated. The residue was chromatographed on silica gel. Elution with dichloromethane containing 1% triethylamine first gave some impurity. Gradually increasing the eluent polarity to dichloromethane/methanol/triethylamine (84:15:1) gave the pure product. The product-containing fractions were combined and evaporated to give a solid which was crystallised from methanol/ethyl acetate to give the title compound, (0.188 g), m.p. 241°–243° C.

Analysis %: Found: C, 58.52; H, 6.36; N, 15.78; $C_{17}H_{22}N_4O_2S$ requires: C, 58.93; H, 6.40; N, 16.17.

EXAMPLE 13

N-{4-[2-[4-(4-Pyridinyl)-1-piperazinyl]acetyl]phenyl}ethanesulphonamide (i) N-[4-Bromoacetylphenyl]ethanesulphonamide

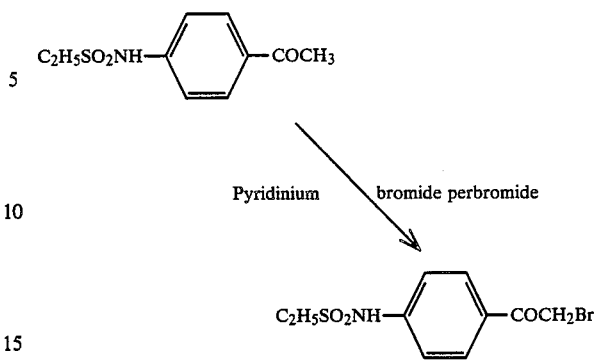

Pyridinium bromide perbromide (7.85 g, 90% purity) was added portionwise to a stirred solution of N-(4-acetylphenyl)ethanesulphonamide in acetic acid (100 ml) at 40° C. and stirring was continued at this temperature for 2 hours. The solution was poured into water and the solid was filtered, washed with water and dried to give the title compound, (6.15 g), pure enough for further reaction.

(ii) N-{4-[2-[4-(4-Pyridinyl)-1-piperazinyl]acetyl]phenyl}ethanesulphonamide

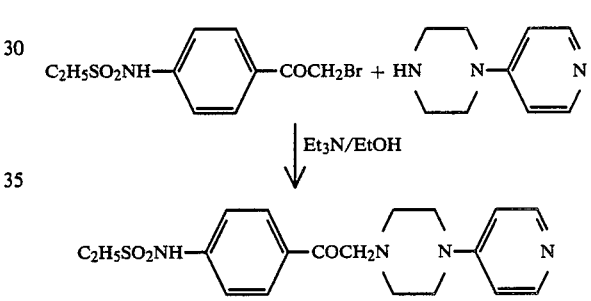

Reaction of the product from part (i) (5.0 g) with 1-(4-pyridinyl)piperazine (2.66 g) according to the method of Example 1 gave the title compound, (2.77 g), m.p. 204°–208° C.

Analysis: Found: C, 57.67; H, 6.21; N, 13.99 $C_{19}H_{24}N_4O_3S$, $0.5H_2O$ requires: C, 57.41; H, 6.34; N, 14.10.

EXAMPLE 14

N-{4-[1-Hydroxy-2-(4-[4-pyridinyl]-1-piperazinyl)ethyl]phenyl}ethanesulphonamide

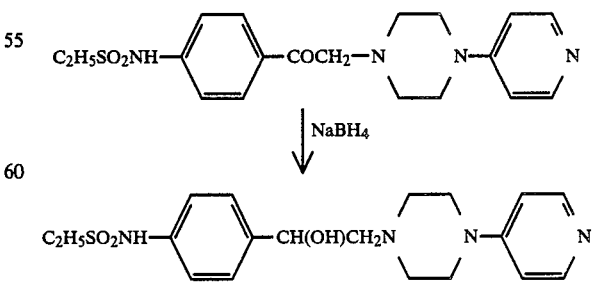

Treatment of the product of Example 13 (0.64 g) with sodium borohydride by the method of Example 2 gave the title compound, (0.21 g), m.p. 186°–188° C.

Analysis %: Found: C, 57.80; H, 6.75; N, 13.82; $C_{19}H_{26}N_4O_3S$, $0.25H_2O$ requires: C, 57.77; H, 6.76; N, 14.19.

EXAMPLE 15

N-{4-[2-(4-[4-Pyridinyl]-1-piperazinyl)acetyl]phenyl}acetamide

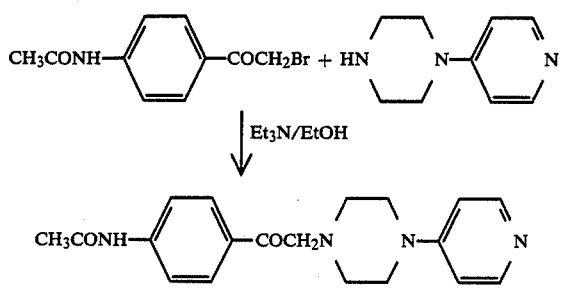

Treatment of 1-(4-pyridinyl)piperazine (10.19 g) with N-[4-bromoacetylphenyl]acetamide (16.0 g) by the method of Example 1 gave the title compound, (10.16 g), m.p. 225°-230° C. (decomp.).

Analysis %: Found: C, 67.54; H, 6.57; N, 16.51; $C_{19}H_{22}N_4O_2$ requires: C, 67.43; H, 6.55; N, 16.56.

EXAMPLE 16

1-(4-Aminophenyl)-2-[4-(4-pyridinyl)-1-piperazinyl]ethanone

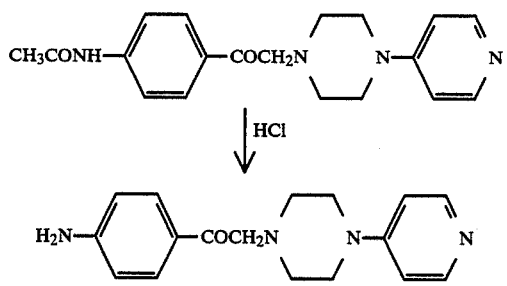

A solution of the product of Example 15 (1.14 g) in 5N hydrochloric acid (114 ml) was heated at 100° C. for 1 hour and then evaporated to ca. 15 ml at 50° C. The cooled solution was made basic (pH 8-9) with sodium bicarbonate and allowed to stand until precipitation was complete. The solid was filtered off, washed with water and dried to give the title compound, (0.80 g), m.p. 128°-131° C.

Analysis %: Found: C, 64.57; H, 6.64; N, 17.50; $C_{17}H_{20}N_4O.H_2O$ requires: C, 64.94; H, 7.05; N, 17.82.

EXAMPLE 17

1-[2-(4-Aminophenyl)-2-hydroxyethyl]-4-(4-pyridinyl)piperazine

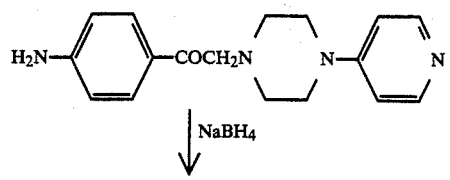

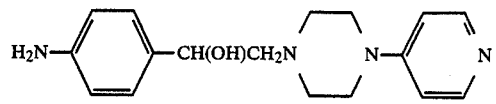

Treatment of the product of Example 16 (4.00 g) with sodium borohydride by the method of Example 2 gave the title compound, (1.88 g), m.p. 201°-203° C.

Analysis %: Found: C, 68.62; H, 7.45; N, 18.89; $C_{17}H_{22}N_4O$ requires: C, 68.43; H, 7.43; N, 18.78.

EXAMPLE 18

N,N-Dimethyl-N'-{4-[1-hydroxy-2-[4-(4-pyridinyl)-1-piperazinyl]ethyl]phenyl}sulphamide

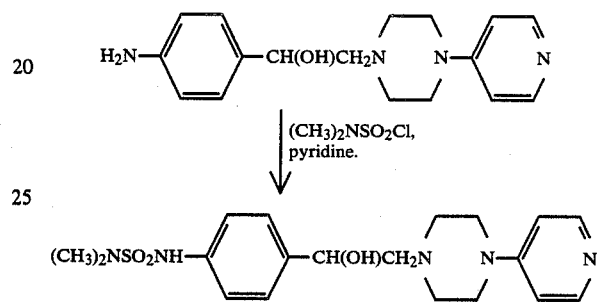

Dimethylsulphamoyl chloride (0.158 g) was added dropwise to a stirred solution of 1-[2-(4-aminophenyl)-2-hydroxyethyl]-4-(4-pyridinyl)piperazine (the product of Example 17) (0.30 g) in pyridine (5 ml) and the mixture was stirred at room temperature for 72 hours. The solvent was evaporated and the residue was stirred with aqueous sodium bicarbonate and the mixture was then extracted several times with dichloromethane. The combined extracts were dried ($Na_2SO_4$) and evaporated to give an oil which was chromatographed on silica gel. Elution with dichloromethane/triethylamine (99:1) gave some impurity and further elution with dichloromethane/methanol/triethylamine (94:5:1) gave the title compound, (0.09 g), m.p. ca. 205° C. (decomp).

Analysis %: Found: C, 54.68; H, 6.65; N, 16.65; $C_{19}H_{27}N_5O_3S$, $0.5 H_2O$ requires: C, 55.00; H, 6.81; N, 16.90.

EXAMPLE 19

N-{4-[2-(4-[3-Pyridinyl]-1-piperazinyl)acetyl]phenyl}methanesulphonamide (i) 1-(3-Pyridinyl)piperazine

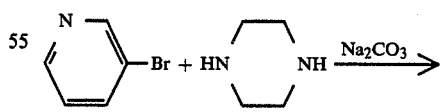

A mixture of 3-bromopyridine (10.0 g), piperazine (11.0 g) and sodium carbonate (10.0 g) in amyl alcohol (30 ml) was heated under reflux for 14 days. The mixture was cooled, filtered, and the residue was washed with ethanol. The combined filtrate and washings were evaporated and the residue was chromatographed on silica gel. Elution with chloroform/methanol/concentrated aqueous ammonia (80:20:1) first gave some impurity followed by the pure product as an oil (2.20 g).

(ii) N-{4-[2-(4-[3-Pyridinyl]-1-piperazinyl)acetyl]phenyl}methanesulphonamide

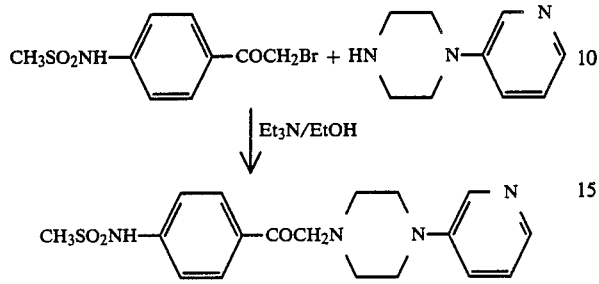

Treatment of 1-(3-pyridinyl)piperazine (0.65 g) with N-[4-(bromoacetyl)phenyl]methanesulphonamide (1.17 g) according to the method of Example 1 gave the title compound, (0.90 g), m.p. 197°–198° C.

Analysis %: Found: C, 57.76; H, 5.90; N, 14.82; $C_{18}H_{22}N_4O_3S$ requires: C, 57.73; H, 5.92; N, 14.96.

EXAMPLE 20

N-{4-[1-Hydroxy-2-(4-[3-pyridinyl]-1-piperazinyl)ethyl]phenyl}methanesulphonamide

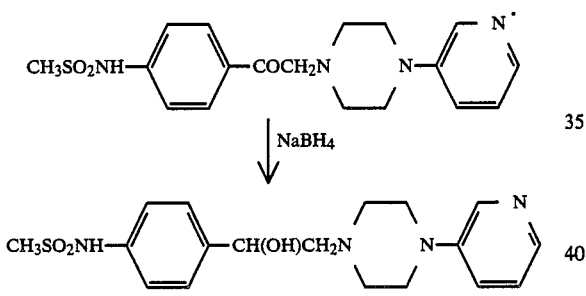

Treatment of the product of Example 19 (0.37 g) with sodium borohydride according to the method of Example 2 gave the title compound (0.19 g), m.p. 194°–195° C.

Analysis %: Found: C, 57.57; H, 6.53; N, 14.79; $C_{18}H_{24}N_4O_3S$ requires: C, 57.43; H, 6.43; N, 14.88.

EXAMPLE 21

N-{4-[2-(4-[1-Methyl-2-imidazolyl]-1-piperazinyl)acetyl]phenyl}methanesulphonamide (i) N-Methyl-[4-formyl-1-piperazinyl]carbothioamide

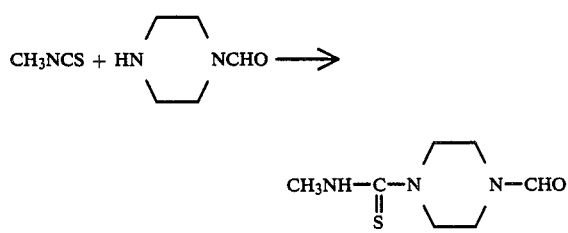

A solution of methyl isothiocyanate (7.30 g) in dichloromethane (40 ml) was added dropwise over 15 minutes to a solution of 1-formylpiperazine (11.4 g) in dichloromethane (120 ml). The mixture was allowed to stand at room temperature for 2 hours and then cooled in ice. The solid was filtered off and crystallised from dichloromethane containing a trace of methanol to give the title compound, (14.6 g), m.p. 164°–165° C.

(ii) 1-(1-Methyl-2-imidazolyl)piperazine

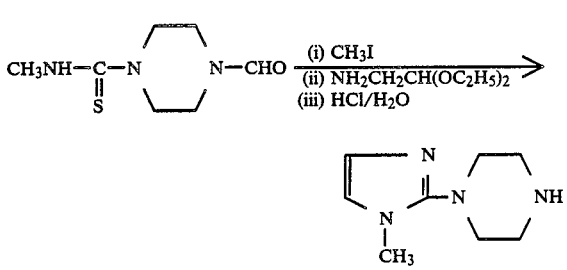

To a solution of N-methyl-[4-formyl-1-piperazinyl]carbothioamide (5.60 g) in methanol (80 ml) was added a solution of iodomethane (4.68 g) in methanol (20 ml). The solution was stirred at room temperature for 18 hours and then evaporated. The residue was dissolved in pyridine and aminoacetaldehyde diethyl acetal (4.40 g) was added. The solution was heated at 100° C. for 6 hours and then evaporated. 2N Hydrochloric acid (50 ml) was added and the solution was heated under reflux for 1½ hours and then evaporated. The residue was dissolved in a small volume of water and the solution was passed down an Amberlite "IRA 400" (Trade Mark) ion exchange column in the $OH^\ominus$ form, using water as the eluent. The solution was collected and evaporated to give a solid which was chromatographed on silica gel. Elution with ethyl acetate/methanol (4:1) gave the title compound, (3.40 g), m.p. 73°–74° C.

The hydrochloric salt had m.p. 237°–238° C.

Analysis %: Found: C, 47.24; H, 7.35; N, 27.53; $C_8H_{14}N_4.HCl$ requires: C, 47.40; H, 7.46; N, 27.64.

(iii) N-{4-[2-(4-[1-Methyl-2-imidazolyl]-1-piperazinyl)acetyl]phenyl}methanesulphonamide

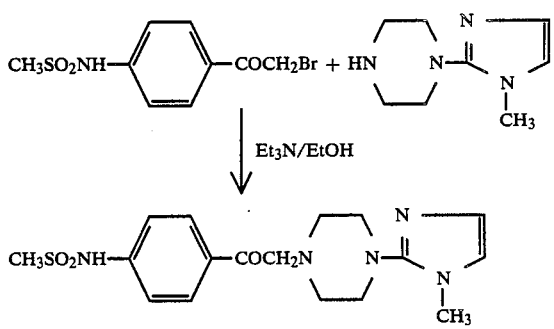

Treatment of 1-(1-methyl-2-imidazolyl)piperazine (0.37 g) with N-[4-bromoacetylphenyl]methanesulphonamide (0.64 g) according to the method of Example 1 gave the title compound, (0.36 g), m.p. 196°–197° C.

Analysis %: Found: C, 53.90; H, 6.24; N, 18.58; $C_{17}H_{23}N_5O_3S$ requires: C, 54.09; H, 6.14; N, 18.56.

EXAMPLE 22

N-{4-[1-Hydroxy-2-(4-[1-methyl-2-imidazolyl]-1-piperazinyl)ethyl]phenyl}methanesulphonamide

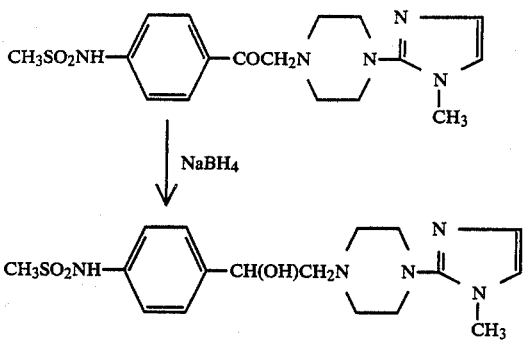

Treatment of the product of Example 21 (0.15 g) with sodium borohydride according to the method of Example 2 gave the title compound, (0.115 g), m.p. 191°–192° C.

Analysis %: Found: C, 53.70; H, 6.61; N, 18.16; $C_{17}H_{25}N_5O_3S$ requires: C, 53.80; H, 6.64; N, 18.46.

EXAMPLE 23

N-{4-[2-(4-[2-Methyl-4-pyridinyl]-1-piperazinyl)acetyl]phenyl}methanesulphonamide
 (i) 1-(2-Methyl-4-pyridinyl)piperazine

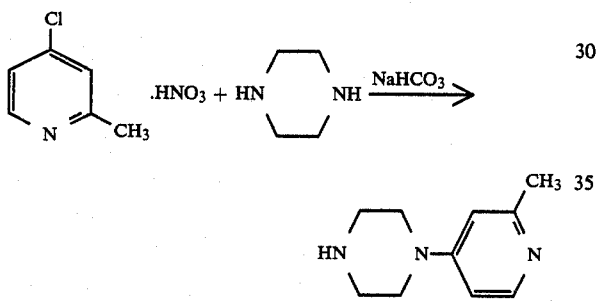

A mixture of 4-chloro-2-methylpyridine nitrate (5.00 g), piperazine (9.00 g) and sodium bicarbonate (6.60 g) in amyl alcohol (60 ml) was heated under reflux for 48 hours and then cooled and washed with a small volume of water. The organic layer was washed with brine (4×25 ml). The combined aqueous layers were washed with ethyl acetate and the combined ethyl acetate and amyl alcohol layers were evaporated. The residue was crystallised from ethyl acetate/hexane to give the title compound (2.80 g), m.p. 93°–94° C.

(ii) N-{4-[2-(4-[2-Methyl-4-pyridinyl]-1-piperazinyl)acetyl]phenyl}methanesulphonamide

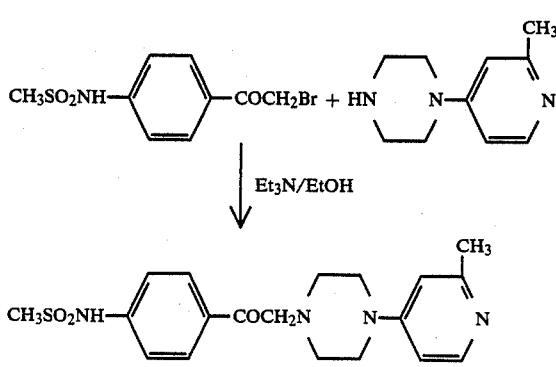

Treatment of 1-[4-(2-methylpyridinyl)]piperazine (0.71 g) with N-[4-bromoacetylphenyl]methanesulphonamide (1.17 g) according to the method of Example 1 gave the title compound, (0.60 g), m.p. 201°–203° C.

Analysis %: Found: C, 58.66; H, 6.25; N, 14.76; $C_{19}H_{24}N_4O_3S$ requires: C, 58.74; H, 6.23; N, 14.42.

EXAMPLE 24

N-{4-[1-Hydroxy-2-(4-[2-methyl-4-pyridinyl]-1-piperazinyl)ethyl]phenyl}methanesulphonamide

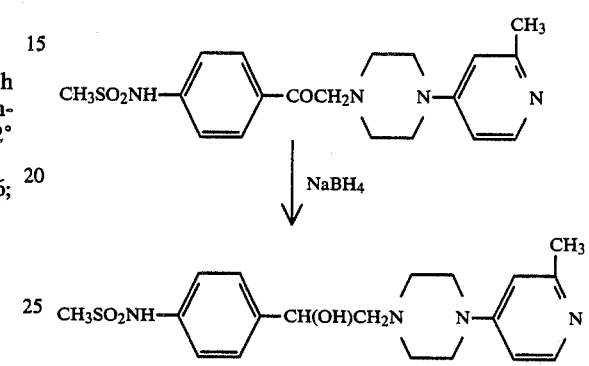

Treatment of the product of Example 23 (0.31 g) with sodium borohydride according to the method of Example 2 gave the title compound, (0.275 g), m.p. 219°–220° C.

Analysis %: Found: C, 58.08; H, 7.09; N, 13.98; $C_{19}H_{26}N_4O_3S$ requires: C, 58.44; H, 6.71; N, 14.35.

EXAMPLE 25

N-{4-[2-(4-[3-Methyl-4-pyridinyl]-1-piperazinyl)acetyl]phenyl}methanesulphonamide
 (i) 1-(3-methyl-4-pyridinyl)piperazine

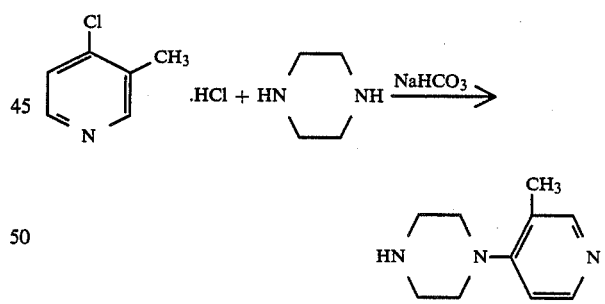

A mixture of 4-chloro-3-methylpyridine hydrochloride (5.80 g), piperazine (12.64 g) and sodium bicarbonate (8.24 g) in n-butanol (100 ml) was heated under reflux for 136 hours and then cooled and filtered. The filtrate was evaporated and the residue was heated at 100° C. under vacuum to remove excess piperazine. The residue was then cooled to give the title compound as a waxy solid, (1.02 g).

The oxalate salt had m.p. 227°–228° C.

Analysis %: Found: C, 53.37; H, 6.42; L N, 15.30; $C_{10}H_{15}N_3.C_2H_2O_4$, 0.25 $H_2O$ requires: C, 53.03; H, 6.49; N, 15.46.

(ii) N-{4-[2-(4-[3-Methyl-4-pyridinyl]-1-piperazinyl)acetyl]phenyl}methanesulphonamide

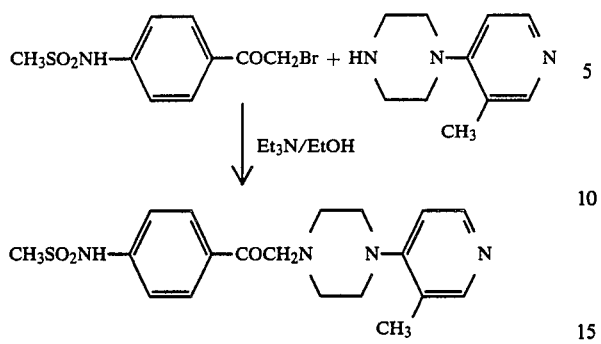

Reaction of the product from part (i) (0.50 g) with N-[4-bromoacetylphenyl]methanesulphonamide (1.10 g) by the method of Example 1 gave the title compound, (0.65 g), m.p. 201°–205° C.

Analysis %: Found: C, 58.40; H, 6.27; N, 14.15; $C_{19}H_{24}N_4O_3S$ requires: C, 58.74; H, 6.23; N, 14.42.

EXAMPLE 26

N-{4-[1-Hydroxy-2-(4-[3-methyl-4-pyridinyl]-1-piperazinyl)ethyl]phenyl}methanesulphonamide

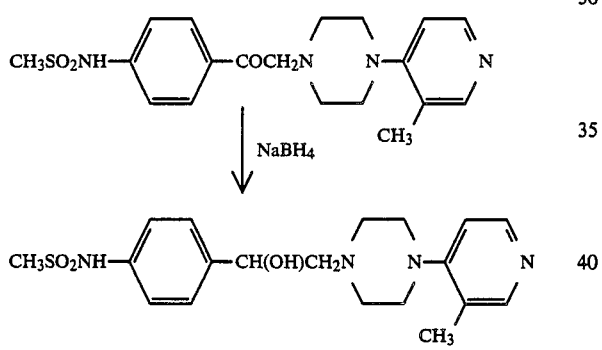

Treatment of the product of Example 25 (0.28 g) and sodium borohydride according to the method of Example 2 gave the title compound, (0.125 g), m.p. 193°–196° C.

Analysis %: Found: C, 58.15; H, 6.67; N, 14.36; $C_{19}H_{26}N_4O_3S$ requires: C, 58.44; H, 6.71; N, 14.35.

EXAMPLE 27

N-{4-[1-Hydroxy-2-(4-[4-amino-2-pyridinyl]-1-piperazinyl)ethyl]phenyl}methanesulphonamide (i) 1-[4-Nitro-2-pyridinyl]piperazine and 1-[2-chloro-4-pyridinyl]piperazine

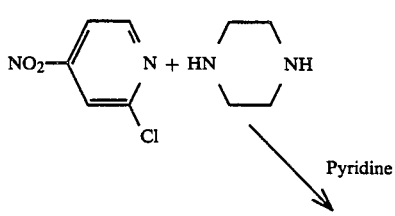

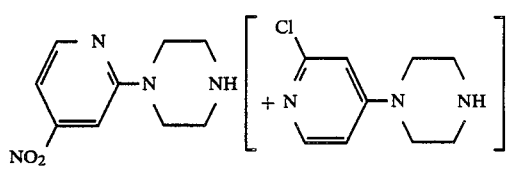

A solution of 2-chloro-4-nitropyridine (4.89 g), and piperazine (7.90 g) in pyridine (90 ml) was heated under reflux for 5 hours and then evaporated. The residue was dissolved in water and the solution was basified with sodium bicarbonate (to pH 8–9) and then continuously extracted with dichloromethane. The extract was dried ($Na_2SO_4$) and evaporated to give an oil which was chromatographed on silica gel. Elution with dichloromethane/methanol/concentrated aqueous ammonia (98:2:1) first gave a solid that was crystallised from ethyl acetate/hexane to give 1-[4-nitro-2-pyridinyl]piperazine (1.21 g), m.p. 92°–93° C.

Analysis %: Found: C, 51.63; H, 5.89; H, 26.82; $C_9H_{12}N_4O_2$ requires: C, 51.91; H, 5.81; N, 26.91.

Further elution of the column gave a solid which was crystallised from ethyl acetate/hexane to give 1-[2-chloro-4-pyridinyl]piperazine, (0.30 g), m.p. 119°–120° C.

Analysis %: Found: C, 54.38; H, 6.04; N, 21.06; $C_9H_{12}ClN_3$ requires: C, 54.68; H, 6.12; N, 21.26.

(ii) N-{4-[2-(4-[4-Nitro-2-pyridinyl]-1-piperazinyl)acetyl]phenyl}methanesulphonamide

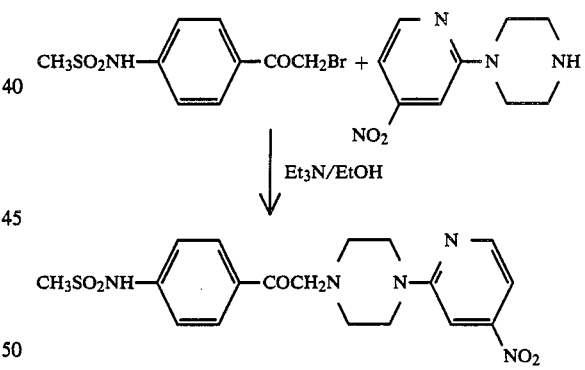

Treatment of 1-[4-nitro-2-pyridinyl]piperazine with N-[4-bromoacetylphenyl]methanesulphonamide according to the method of Example 1 gave the title compound which was used directly in the next stage.

(iii) N-{4-[2-(4-[4-Amino-2-pyridinyl]-1-piperazinyl)acetyl]phenyl}methanesulphonamide

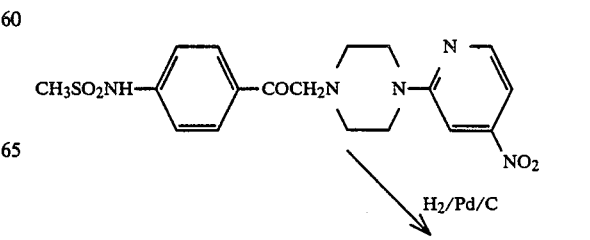

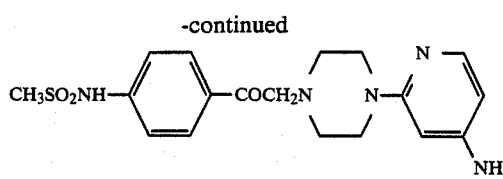

A mixture of the product of part (ii) (0.70 g) and 5% palladium/carbon (0.07 g) in ethanol was hydrogenated at 3.5 atmospheres and 20° C. The catalyst was filtered off and the filtrate was evaporated to give a solid which was chromatographed on silica gel. Elution with dichloromethane/methanol (98:2) gave the title compound as a solid which was used directly in the next stage.

(iv) N-{4-[1-Hydroxy-2-(4-[4-amino-2-pyridinyl]-1-piperazinyl)ethyl]phenyl}methanesulphonamide

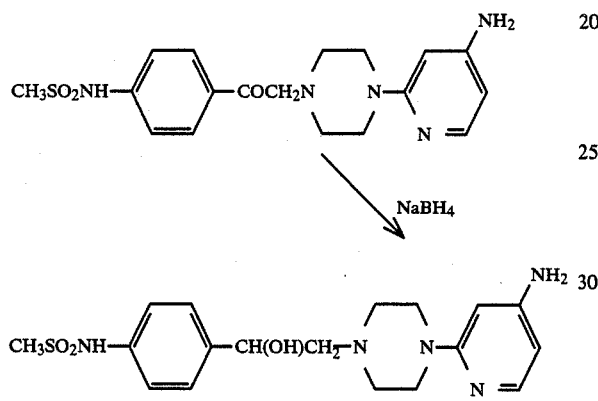

Treatment of the product of part (iii) (0.10 g) with sodium borohydride by the method of Example 2 gave the title compound, (0.06 g), m.p. 223°–226° C.

Analysis %: Found: C, 54.98; H, 6.52; N, 17.49; $C_{18}H_{25}N_5O_3S$ requires: C, 55.22; H, 6.44; N, 17.89.

EXAMPLE 28

N-{4-[1-Hydroxy-2-(4-[4-amino-3-pyridinyl]-1-piperazinyl)ethyl]phenyl}methanesulphonamide (i) 4-Nitro-3-(1-piperazinyl)pyridine-N-oxide

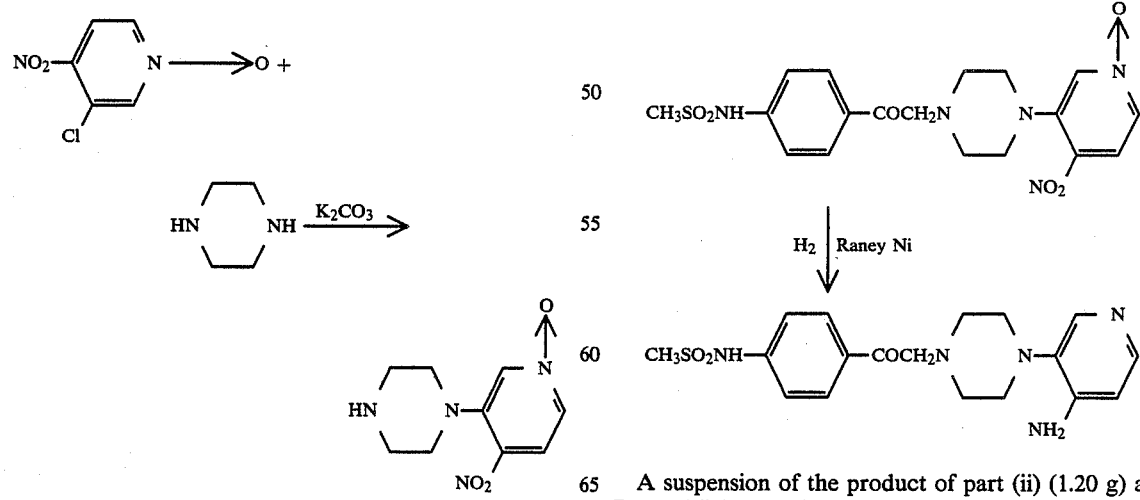

A mixture of 3-chloro-4-nitropyridine-N-oxide (3.00 g), piperazine (6.00 g) and potassium carbonate (3.00 g) in n-butanol (50 ml) was heated under reflux with stirring for 2 hours and then evaporated. The residue was partitioned between dichloromethane and 10% sodium carbonate solution. The aqueous layer was extracted several times with dichloromethane and the combined organic layers were dried ($Na_2SO_4$) and evaporated to give the title compound, (3.0 g), pure enough for further reaction. A sample crystallised from ethanol/ethyl acetate had m.p. 167°–169° C.

Analysis %: Found: C, 48.36; H, 5.51; N, 24.77; $C_9H_{12}N_4O_3$ requires: C, 48.21; H, 5.40; N, 24.99.

(ii) N-{4-[2-(4-[4-Nitro-1-oxido-3-pyridinyl]-1-piperazinyl)acetyl]phenyl}methanesulphonamide

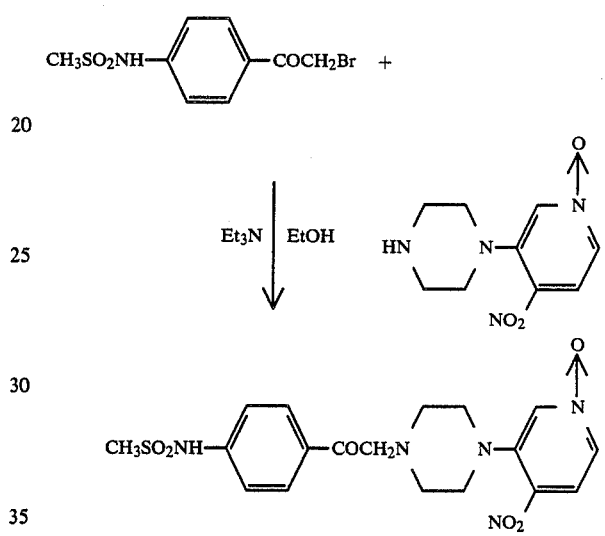

Treatment of the product of part (i) (1.50 g) with N-[4-bromoacetylphenyl]methanesulphonamide (2.40 g) according to the method of Example 1 gave the title compound, (1.40 g), m.p. 202° C. (decomp).

Analysis %: Found: C, 49.26; H, 4.47; N, 15.83; $C_{18}H_{21}N_5O_6S$ requires: C, 49.64; H, 4.86; N, 16.08.

(iii) N-{4-[2-(4-[4-Amino-3-pyridinyl]-1-piperazinyl)acetyl]phenyl}methanesulphonamide

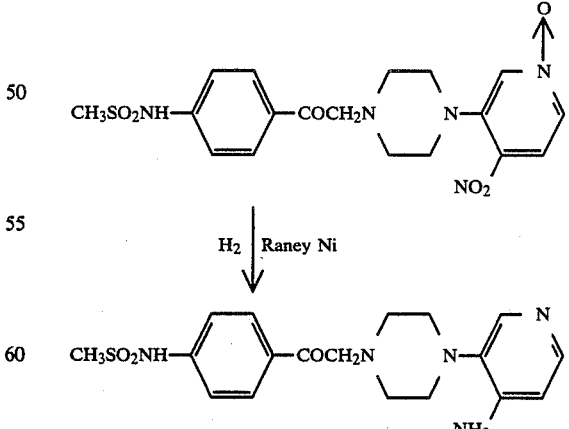

A suspension of the product of part (ii) (1.20 g) and Raney Ni (0.12 g) in methanol (180 ml) and acetic acid (20 ml) was hydrogenated at 2 atmospheres and 20° C. When no further hydrogen was taken up the catalyst was filtered off and the filtrate was evaporated to give the crude product which was used directly in the next stage. (iv) N-{4-[1-Hydroxy-2-(4-[4-amino-3-pyridinyl]-1-piperazinyl)ethyl]phenyl}methanesulphonamide

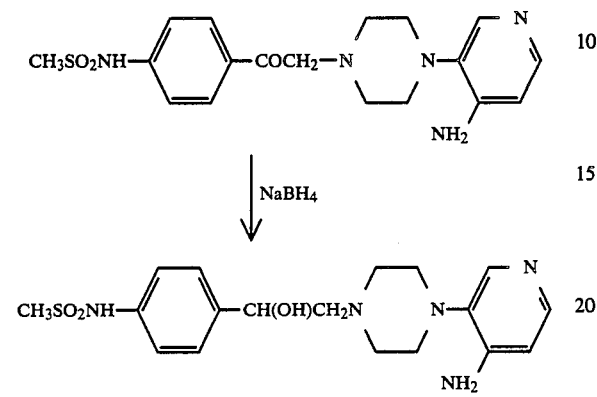

The product of part (iii) (0.70 g) was treated with sodium borohydride according to the method of Example 2 to give the title compound, (0.40 g), m.p. 245°–247° C.

Analysis %: Found: C, 55.52; H, 6.41; N, 17.95; $C_{18}H_{25}N_5O_3S$ requires: C, 55.22; H, 6.44; N, 17.89.

EXAMPLE 29

N-{4-[1-Hydroxy-2-(4-[2-amino-4-pyridinyl]-1-piperazinyl)ethyl]phenyl}methanesulphonamide (i) 4-[4-Phenylmethyl-1-piperazinyl]-pyridine-2-carboxylic acid hydrazide

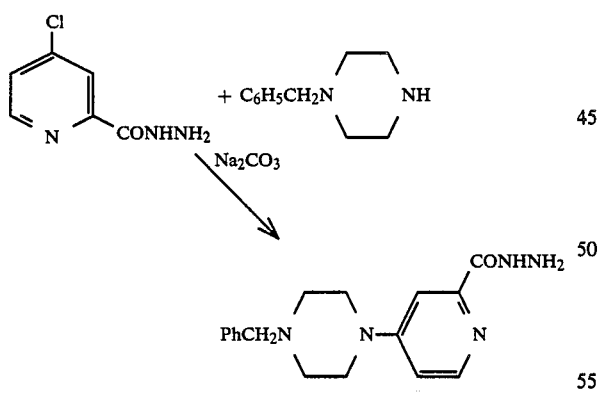

A mixture of 4-chloropyridine-22-carboxylic acid hydrazide (1.71 g), 1-phenylmethylpiperazine (1.76 g) and sodium bicarbonate (1.1 g) in (10 ml) was heated under reflux with stirring for 24 hours and then evaporated. The residue was triturated with water and the solid was filtered off, washed with water and crystallised from ethanol to give the title compound, 1.30 g, m.p. 140°–142° C.

(ii) N-{4-[4-Phenylmethyl-1-piperazinyl]-2-pyridinyl}-carbamic acid ethyl ester

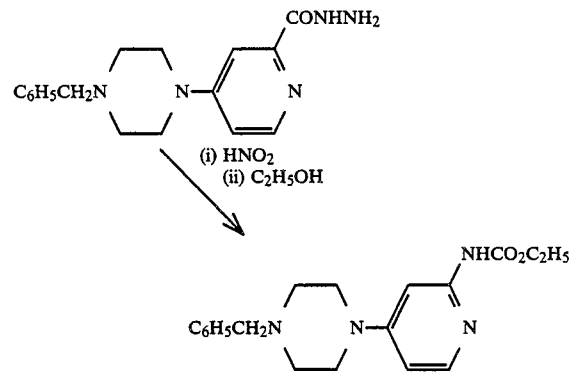

A solution of sodium nitrite (2.63 g) in water (18 ml) was added dropwise over 15 minutes to a stirred solution of the product of part (i) (10.77 g) in 2N hydrochloric acid (100 ml) at 0° C. The solution was stirred at 0° C. for 1 hour and then made basic (to pH 8–9) with sodium bicarbonate. The resulting suspension was extracted several times with dichloromethane and the combined extracts were dried ($Na_2SO_4$) and evaporated in vacuo at room temperature. The residual gum was dissolved in ethanol (120 ml) and the solution was heated under reflux for 2 hours and then concentrated to ca. 50 ml. The mixture was allowed to stand and the solid was filtered off and dried to give the title compound, (5.96 g), m.p. 156°–157° C.

Analysis %: Found: C, 66.89; H, 7.25; N, 16.31; $C_{19}H_{24}N_4O_2$ requires: C, 67.06; H, 7.06; N, 16.47.

(iii) N-{4-(1-Piperazinyl)-2-pyridinyl}carbamic acid ethyl ester

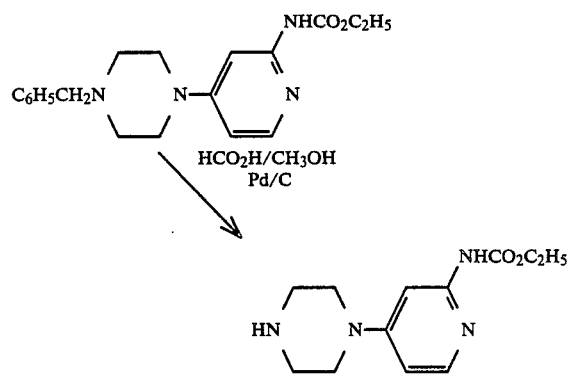

10% Palladium/carbon (5.0 g) was added portionwise over 30 minutes to a stirred solution of the product of part (ii) (5.82 g) in a 4.4% solution of formic acid in methanol (240 ml). The mixture was stirred vigorously at room temperature for 18 hours and then filtered. The catalyst was boiled with methanol and filtered, and the combined filtrates were evaporated to give the title compound (3.24 g), m.p. 156°–157° C.

Analysis %: Found: C, 57.34; H, 7.47; N, 22.54; $C_{12}H_{18}N_4O_2$ requires: C, 57.60; H, 7.20; N, 22.40.

(iv) N-{4-[2-(4-[2-Ethoxycarbonylamino-4-pyridinyl]-1-piperazinyl)acetyl]phenyl}methanesulphonamide

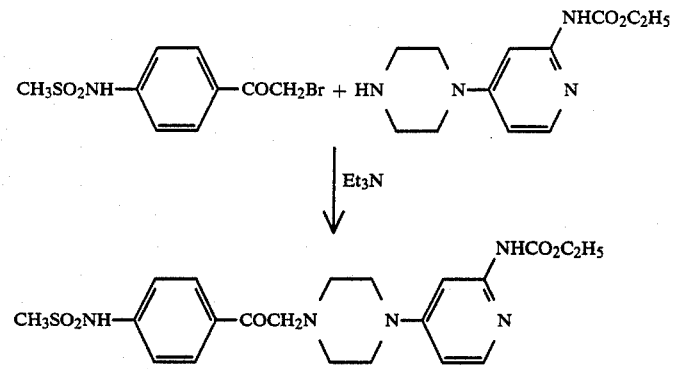

Treatment of the product of part (iii) (4.10 g) with N-(4-bromoacetylphenyl)methanesulphonamide (4.85 g) according to the method of Example 1 gave the title compound, (5.08 g), m.p. 215°–6° C. (with decomposition) (from chloroform/methanol, 4:1).

(v) N-{4-[1-Hydroxy-2-(4-[2-ethoxycarbonylamino-4-pyridinyl]-1-piperazinyl)ethyl]phenyl}methanesulphonamide

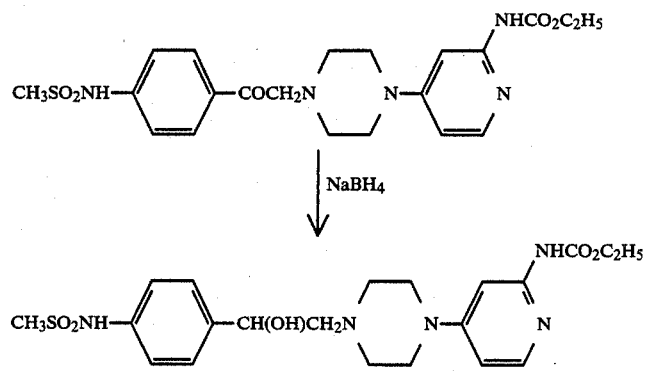

Treatment of the product of part (iv) (4.95 g) with sodium borohydride according to the method of Example 2 gave the title compound, (4.51 g), m.p. 210°–215° C. (with decomposition) (from ethanol), used directly in the next stage.

(vi) N-{4-[1-Hydroxy-2-(4-[2-amino-4-pyridinyl]-1-piperazinyl)ethyl]phenyl}methanesulphonamide

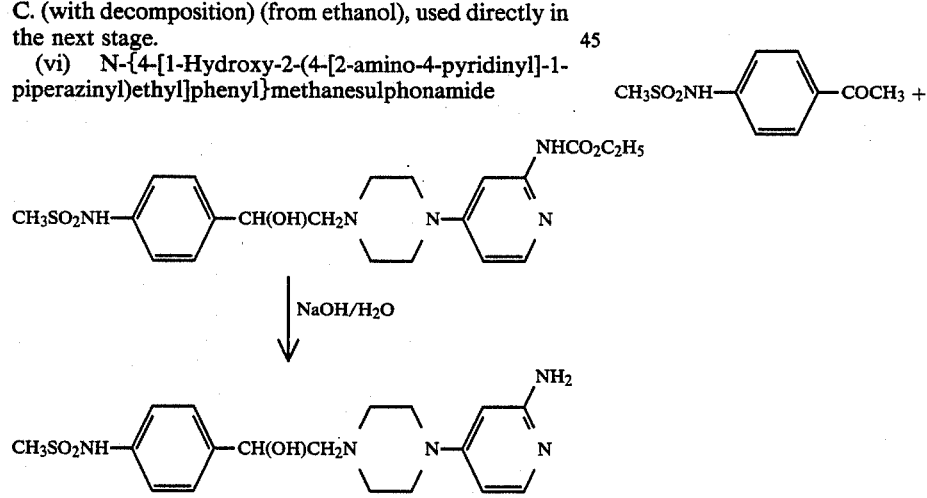

A mixture of the product of part (v) above (30 mg), 40% aqueous sodium hydroxide (3 ml) and ethanol (0.3 ml) was heated under reflux for 1 hour. The solution was cooled, just acidified with 2N hydrochloric acid and then made basic with sodium bicarbonate (to pH 8–9). The mixture was extracted several times with dichloromethane and the combined extracts were dried (Na$_2$SO$_4$) and evaporated to give the title compound, (13 mg), m.p. 226°–227° C. (from ethanol).

Analysis %: Found: C, 54.18; H, 6.57; N, 17.05; C$_{18}$H$_{25}$N$_5$O$_3$S, 0.5 H$_2$O requires: C, 54.00; H, 6.50; N, 17.50.

EXAMPLE 30

N-{4-[3-(4-[4-Pyridinyl]-1-piperazinyl)propionyl]phenyl}methanesulphonamide

-continued

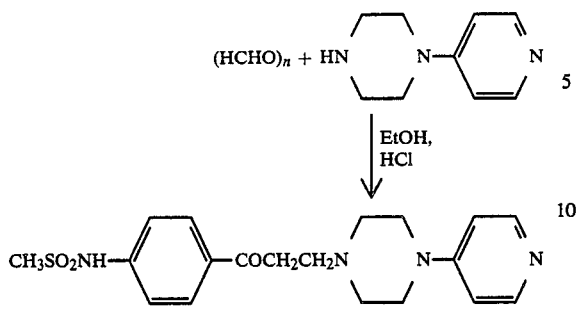

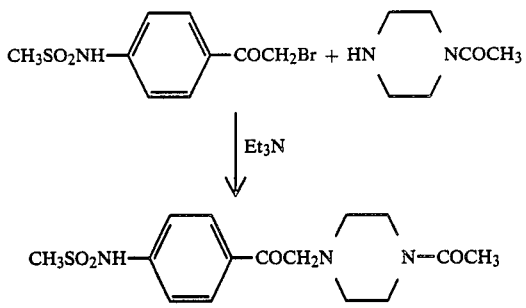

A solution of 1-(4-pyridinyl)piperazine (0.82 g) in ethanol (40 ml) was made just acidic with concentrated hydrochloric acid and N-(4-acetylphenyl)methanesulphonamide (1.07 g) and paraformaldehyde (0.18 g) were added and the mixture was heated under reflux for 44 hours. Further quantities of paraformaldehyde were added after 4 hours (0.18 g) and 24 hours (0.36 g). The solvent was evaporated and water (20 ml) was added. The solution was made basic with solid sodium bicarbonate (pH 8–9) and continuously extracted with dichloromethane for 13 hours. The organic layer was dried ($Na_2SO_4$) and evaporated, and the residue was chromatographed on silica gel. The column was eluted with dichloromethane containing 1% methanol, gradually increasing the proportion of methanol to 5%. Impurity was eluted first followed by pure product. The product-containing fractions were evaporated to give the title compound as a solid, (0.40 g), m.p. 218°–220° C. (from methanol).

Analysis %: Found: C, 58.45; H, 6.26; N, 14.15; $C_{19}H_{24}N_4O_3S$ requires: C, 58.74; H, 6.23; N, 14.42.

EXAMPLE 31

N-{4-[1-Hydroxy-3-(4-[4-pyridinyl]-1-piperazinyl)-propyl]phenyl}methanesulphonamide

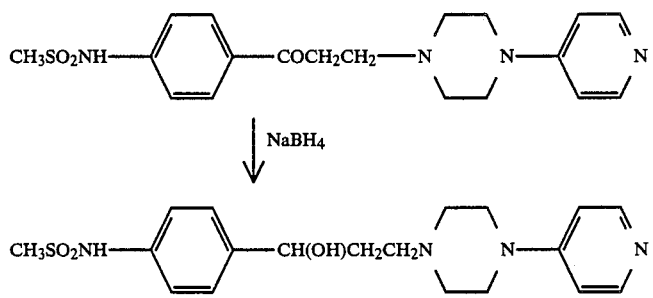

Reduction of the product of Example 30 (0.155 g) with sodium borohydride by the method of Example 2 gave the title compound, (0.09 g), m.p. 195°–196° C.

Analysis %: Found: C, 58.15; H, 6.80; N, 14.09; $C_{19}H_{26}N_4O_3S$ requires: C, 58.44; H, 6.71; N, 14.35.

EXAMPLE 32

N-(4-{1-Hydroxy-2-[4-(4-pyridinyl)-1-piperazinyl]ethyl}phenyl)methanesulphonamide (i) N-{4-[(4-acetyl-1-piperazinyl)acetyl]phenyl}methanesulphonamide A solution of N-acetylpiperazine (100 g) in industrial methylated spirits (IMS) (228 ml) containing triethylamine (82.7 g) was added to a suspension of N-[4-bromoacetylphenyl]methanesulphonamide (228 g) in IMS (556 ml) over 20 minutes to give a clear solution.

The exothermic temperature of 45° C. was sustained for ½ hour during which time the product began to precipitate. After maintaining the reaction mixture at −5° C. for 1 hour the product was filtered off, washed with water (2×1 l.) and dried at 70° in vacuo to give the title compound, (230.9 g), m.p. 156°–158° C.

Analysis %: Found: C, 52.92; H, 6.26; N, 12.26; $C_{15}H_{21}N_3O_4S$ requires: C, 53.03; H, 6.19; N, 12.37.

(ii) N-(4-{1-Hydroxy-2-[4-(4-pyridinyl)-1-piperazinyl]ethyl}phenyl)methanesulphonamide

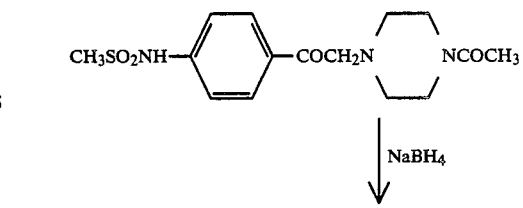

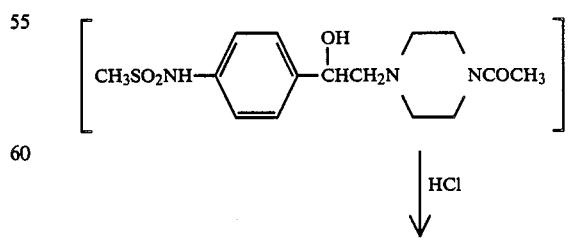

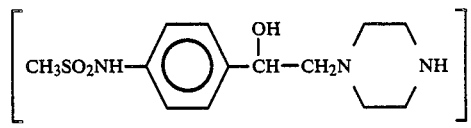

-continued

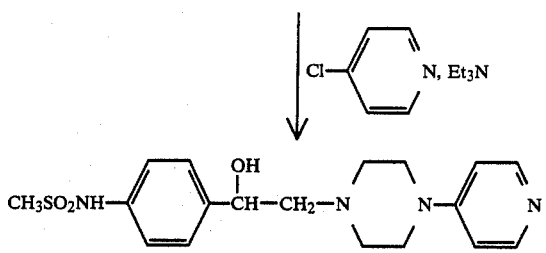

A suspension of N-{4-[(4-acetyl-1-piperazinyl)acetyl]phenyl}methanesulphonamide (225 g) in water (675 ml) was heated with stirring to 95°–100° C. and to this was added over ½ hour a solution of sodium borohydride (76.6 g) in water (225 ml) containing 40% caustic solution (4 ml). Concentrated hydrochloric acid (400 ml) was added soon after the addition of the borohydride solution and the whole was refluxed for 1 hour to remove the N-acetyl group. The reaction was then cooled to 50° C. to give a suspension of the hydrochloride salt. Addition, with cooling, of 40% caustic solution (300 ml) gave a solution of the free base. This was filtered to remove some insoluble inorganic salts, and the aqueous solution was distilled with isoamyl alcohol (750 ml) under Dean-Stark conditions to remove water. This left a suspension of N-{4-[1-hydroxy-2-(1-piperazinyl)ethyl]phenyl}methanesulphonamide in isoamyl alcohol.

To this suspension was added a solution of 4-chloropyridine in isoamyl alcohol prepared from 4-chloropyridine hydrochloride (99.5 g) on basification with 40% caustic solution and extraction with isoamyl alcohol (3×100 ml). After addition of triethylamine (132 g) the whole was refluxed under nitrogen at 115°–120° C. for 24 hours. Isoamyl alcohol was removed by steam distillation, and I.M.S. (250 ml) and 40% caustic solution were added to raise the pH to 13 to give a brown solution. Reduction in pH to 8.5 with concentrated hydrochloric acid and granulation provided 215 g of the title compound.

For purification, this was digested in I.M.S. at reflux for 1 hour, the suspension was cooled and the product filtered off (183.8 g). The purified products had identical infrared and nuclear magnetic resonance spectra to the product of Example 2.

We claim:
1. A piperazinyl-substituted pyridine or imidazole compound of the formula:

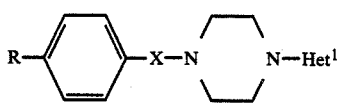

or a pharmaceutically acceptable salt thereof, wherein "Het$^1$" is selected from (a) a 3- or 4-pyridinyl group optionally substituted by one or two substituents each independently selected from $C_1$–$C_4$ alkyl and amino, (b) a 2-pyridinyl group substituted by an amino group and (c) a 2-imidazolyl group optionally substituted by one or two $C_1$–$C_4$ alkyl groups; R is selected from (a) —NHSO$_2$R$^3$ where R$^3$ is $C_1$–$C_4$ alkyl, $C_3$–$C_7$ cycloalkyl or —NR$^1$R$^2$ wherein R$^1$ and R$^2$ are each independently hydrogen or $C_1$–$C_4$ alkyl, (b) —SO$_2$NR$^1$R$^2$ where R$^1$ and R$^2$ are each independently hydrogen or $C_1$–$C_4$ alkyl, (c) nitro, (d) amino and (e) acetamido; and X is a group of the formula —(CH$_2$)$_m$— where m is an integer of from one to four, inclusive, or it is —CO(CH$_2$)$_n$— or —CH(OH)(CH$_2$)$_n$— where n is one, two or three.

2. A compound as claimed in claim 1 wherein "Het$^1$" is selected from (a) a 3- or 4-pyridinyl group optionally substituted by an amino or methyl group, (b) a 2-pyridinyl group substituted by an amino group and (c) a 2-imidazolyl group substituted by a methyl group.

3. A compound as claimed in claim 2 wherein "Het$^1$" is 3-pyridinyl, 4-amino-3-pyridinyl, 4-pyridinyl, 2-methyl-4-pyridinyl, 3-methyl-4-pyridinyl, 2-amino-4-pyridinyl, 4-amino-2-pyridinyl or 1-methyl-imidazol-2-yl.

4. A compound as claimed in claim 3 wherein "Het$^1$" is 4-pyridinyl, 2-amino-4-pyridinyl or 4-amino-2-pyridinyl.

5. A compound as claimed in claim 1 wherein R is selected from (a) —NHSO$_2$R$^3$ where R$^3$ is $C_1$–$C_4$ alkyl or —N($C_1$–$C_4$ alkyl)$_2$, (b) —SO$_2$NHR$^1$ where R$^1$ is hydrogen or $C_1$–$C_4$ alkyl, (c) nitro, (d) amino and (e) acetamido.

6. A compound as claimed in claim 5 wherein R is —NHSO$_2$CH$_3$, —NHSO$_2$CH$_2$H$_5$, —NHSO$_2$N(CH$_3$)$_2$, —SO$_2$NH$_2$, —SO$_2$NHCH$_3$, —NO$_2$, —NH$_2$ or —NHCOCH$_3$.

7. A compound as claimed in claim 6 wherein R is —NHSO$_2$CH$_3$, —SO$_2$NH$_2$ or —SO$_2$NHCH$_3$.

8. A compound as claimed in claim 1 wherein X is —CH$_2$—, —(CH$_2$)$_2$—, —COCH$_2$—, —CO(CH$_2$)$_2$—, —CH(OH)CH$_2$— or —CH(OH)(CH$_2$)$_2$—.

9. A compound as claimed in claim 8 wherein X is —COCH$_2$— or —CH(OH)CH$_2$—.

10. A compound as claimed in claim 1 wherein "Het$^1$" is selected from (a) a 3- or 4-pyridinyl group optionally substituted by an amino or methyl group, (b) a 2-pyridinyl group substituted by an amino group and (c) 2-imidazolyl group substituted by a methyl group; R is selected from (a) —NHSO$_2$R$^3$ where R$^3$ is $C_1$–$C_4$ alkyl or —N($C_1$–$C_4$)$_2$, (b) —SO$_2$NHR$^1$ where R$^1$ is hydrogen or $C_1$–$C_4$ alkyl, (c) nitro, (d) amino and (e) acetamido; and X is —CH$_2$—, —(CH$_2$)$_2$—, —COCH$_2$—, —CO(CH$_2$)$_2$—, —CH(OH)CH$_2$— or CH(OH)(CH$_2$)$_2$—.

11. A compound as claimed in claim 10 wherein "Het$^1$" is 3-pyridinyl, 4-amino-3-pyridinyl, 4-pyridinyl, 2-methyl-4-pyridinyl, 3-methyl-4-pyridinyl, 2-amino-4-pyridinyl, 4-amino-2-pyridinyl or 1-methyl-imidazol-2-yl; R is —NHSO$_2$CH$_3$, —NHSO$_2$C$_2$H$_5$, —NHSO$_2$N—(CH$_3$)$_2$, —SO$_2$NH$_2$, —SO$_2$NHCH$_3$, —NO$_2$, —NH$_2$ or —NHCOCH$_3$; and X is —COCH$_2$— or —CH(OH)CH$_2$—.

12. A compound as claimed in claim 11 wherein "Het$^1$" is 4-pyridinyl, 2-amino-4-pyridinyl or 4-amino-2-pyridinyl.

13. A compound as claimed in claim 11 wherein R is —NHSO$_2$CH$_3$, —SO$_2$NH$_2$ or —SO$_2$NHCH$_3$.

14. A compound as claimed in claim 1 wherein "Het$^1$" is a 3- or 4-pyridinyl group optionally substituted by one or two substituents each independently selected from $C_1$–$C_4$ alkyl and amino; R is selected from (a) —NHSO$_2$R$^3$ where R$^3$ is $C_1$–$C_4$ alkyl, $C_3$–$C_7$ cycloalkyl or —NR$^1$R$^2$ wherein R$^1$ and R$^2$ are each independently hydrogen or $C_1$–$C_4$ alkyl, (b) —SO$_2$NR$^1$R$^2$ where R$^1$ and R$^2$ are each independently hydrogen or $C_1$–$C_4$ alkyl, (c) nitro and (d) amino; and X is a group of the formula —(CH$_2$)$_m$— where m is an integer of from one to four, inclusive, or it is —CO(CH$_2$)$_n$— or —CH(OH)(CH$_2$)$_n$— where n is one, two or three.

15. A compound as claimed in claim 14 wherein "Het$^1$" is 4-pyridinyl or 2-amino-4-pyridinyl.

16. A compound as claimed in claim 14 wherein R is —NHSO$_2$CH$_3$, —NHSO$_2$C$_2$H$_5$, —NHSO$_2$N(CH$_3$)$_2$, —SO$_2$NH$_2$, —SO$_2$NHCH$_3$, NO$_2$ or NH$_2$.

17. A compound as claimed in claim 16 wherein R is —NHSO$_2$CH$_3$, —SO$_2$NH$_2$ or —SO$_2$NHCH$_3$.

18. A compound as claimed in claim 14 wherein X is —CH$_2$—, —(CH$_2$)$_2$—, —COCH$_2$—, —CO(CH$_2$)$_2$, —CH(OH)CH$_2$ or —CH(OH)(CH$_2$)$_2$—.

19. A compound as claimed in claim 18 wherein X is —COCH$_2$— or —CH(OH)CH$_2$—.

20. A compound as claimed in claim 14 wherein "Het$^1$" is 4-pyridinyl or 2-amino-4-pyridinyl; R is —NHSO$_2$CH$_3$, —NHSO$_2$C$_2$H$_5$, —NHSO$_2$N(CH$_3$)$_3$, —SO$_2$NH$_2$, —SO$_2$NHCH$_3$, NO$_2$ or NH$_2$; and X is —CH$_2$—, —(CH$_2$)$_2$—, —COCH$_2$—, —CO(CH$_2$)$_2$—, —CH(OH)CH$_2$— or —CH(OH)(CH$_2$)$_2$—.

21. A compound as claimed in claim 20 wherein R is —NHSO$_2$CH$_3$, —SO$_2$NH$_2$ or —SO$_2$NHCH$_3$, and X is —COCH$_2$— or —CH(OH)CH$_2$—.

22. N-{4-[1-Hydroxy-2-(4-[4-pyridinyl]-1-piperazinyl)ethyl]phenyl}methanesulphonamide.

23. A pharmaceutical composition comprising a pharmaceutically acceptable carrier or diluent and an effective anti-arrhythmic amount of a compound as claimed in claim 1.

24. A method for preventing or reducing cardiac arrythmias in the treatment of a subject afflicted with an impaired cardiac pump function, which comprises administering to said subject an effective anti-arrhythmic amount of a compound as claimed in claim 1.

25. A piperazinyl-substituted pyridine compound of the formula:

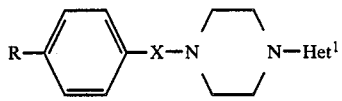

wherein
"Het$^2$" is a 2-, 3- or 4-pyridinyl group substituted by a nitro group, or an N-oxide derivative thereof, or a 2-, 3- or 4-pyridinyl group substituted by a group of the formula —NHCOO(C$_1$-C$_4$ alkyl);
R is selected from (a) —NHSO$_2$R$^3$ where R$^3$ is C$_1$-C$_4$ alkyl, C$_3$-C$_7$ cycloalkyl or —NR$^1$R$^2$ wherein R$^1$ and R$^2$ are each independently hydrogen or C$_1$-C$_4$ alkyl, (b) —SO$_2$NR$^1$R$^2$ where R$^1$ and R$^2$ are each independently hydrogen or C$_1$-C$_4$ alkyl, (c) nitro, (d) amino and (e) acetamido; and
X is a group of the formula —(CH$_2$)$_m$— where m is an integer of from one to four, inclusive, or it is —CO(CH$_2$)$_n$— or —CH(OH)(CH$_2$)$_n$— where n is one, two or three.

26. A compound as claimed in claim 25 wherein "Het$^2$" is 4-nitro-1-oxido-3-pyridinyl, 2-ethoxycarbonylamino-4-pyridinyl or 4-nitro-2-pyridinyl.

27. A 4-substituted piperazine compound of the formula:

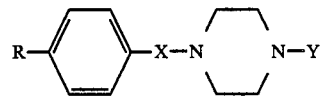

wherein
R is selected from (a) —NHSO$_2$R$^3$ where R$^3$ is C$_1$-C$_4$ alkyl, C$_3$-C$_7$ cycloalkyl or —NR$^1$R$^2$ wherein R$^1$ and R$^2$ are each independently hydrogen or C$_1$-C$_4$ alkyl, (b) —SO$_2$NR$^1$R$^2$ where R$^1$ and R$^2$ are each independently hydrogen or C$_1$-C$_4$ alkyl, (c) nitro, (d) amino and (e) acetamido;
X is a group of the formula —(CH$_2$)$_m$— where m is an integer of from one to four, inclusive, or it is —CO(CH$_2$)$_n$— or —CH(OH)(CH$_2$)$_n$— where n is one, two or three; and
Y is hydrogen or an amino-protecting group.

28. A compound as claimed in claim 27 wherein the amino-protecting group is acetyl, formyl or benzyl.

* * * * *